(12) United States Patent
Jakob-Roetne et al.

(10) Patent No.: US 8,415,379 B2
(45) Date of Patent: *Apr. 9, 2013

(54) PYRIDINES

(75) Inventors: Roland Jakob-Roetne, Inzlingen (DE); Matthew C. Lucas, Verona, NJ (US); Andrew Thomas, Binningen (CH)

(73) Assignees: Hoffmann-La Roche Inc., Nutley, NJ (US); Roche Palo Alto LLC, Palo Alto, CA (US)

( * ) Notice: Subject to any disclaimer, the term of this patent is extended or adjusted under 35 U.S.C. 154(b) by 279 days.

This patent is subject to a terminal disclaimer.

(21) Appl. No.: 12/768,762

(22) Filed: Apr. 28, 2010

(65) Prior Publication Data

US 2010/0286132 A1 Nov. 11, 2010

(30) Foreign Application Priority Data

May 5, 2009 (EP) ..................................... 09159457

(51) Int. Cl.
*A61K 31/443* (2006.01)
*C07D 413/14* (2006.01)

(52) U.S. Cl.
USPC .......................................... 514/333; 546/256

(58) Field of Classification Search .................. 546/256; 514/333
See application file for complete search history.

(56) References Cited

U.S. PATENT DOCUMENTS

| | | | |
|---|---|---|---|
| 4,639,266 A | 1/1987 | Heubach et al. | |
| 2003/0055085 A1 | 3/2003 | Wagener et al. | |
| 2004/0006226 A1 | 1/2004 | Ladduwahetty et al. | |

FOREIGN PATENT DOCUMENTS

| | | |
|---|---|---|
| DE | 3525205 | 3/1986 |
| GB | 2336589 | 10/1999 |
| JP | 2007230909 | 9/2007 |
| WO | 0129015 | 4/2001 |
| WO | 0134603 | 5/2001 |
| WO | 0250062 | 6/2002 |
| WO | 0281474 | 10/2002 |
| WO | 0304027 | 1/2003 |
| WO | 0315771 | 2/2003 |
| WO | 0344017 | 5/2003 |
| WO | 2004048349 | 6/2004 |
| WO | 2005014553 | 2/2005 |
| WO | 2005118568 | 12/2005 |
| WO | 2005123672 | 12/2005 |
| WO | 2006037480 | 4/2006 |
| WO | 2006044617 | 4/2006 |
| WO | 2006069155 | 6/2006 |
| WO | 2007009275 | 1/2007 |
| WO | 2007/039389 | 4/2007 |
| WO | 2007039389 | 4/2007 |
| WO | 2007052843 | 5/2007 |
| WO | 2007076260 | 7/2007 |
| WO | 2007092751 | 8/2007 |
| WO | 2008025539 | 3/2008 |
| WO | 2008025540 | 3/2008 |

OTHER PUBLICATIONS

Ettmayer et al. "Lessons Learned from Marketed and Investigational Prodrugs." J. Med. Chem., (2004), 47(10): 2393-2404.*
Stella, Valentino. "Prodrugs as therapeutics." Expert Opin. Ther. Patents (2004), 14(3): 277-280.*
Testa, Bernard. "Prodrug research: futile or fertile?" Biochemical Pharmacology, 68 (2004): 2097-2106.*
Balant ed in Wolff et al. Burger's Medicinal Chemistry and Drug Discovery. 5th ed. vol. 1: Principles and Practice. pp. 949-982.*
International Search Report by EPO for PCT/EP2010/0556975 mailed Aug. 17, 2010.
McNamara et al., Psychobiology (1993), vol. 21, pp. 101-108.
Goodman et al., Tetrahedron (1999) vol. 55 pp. 15067-15070.
Roy et al., Synthesis, 2003 pp. 1347-1356.
White, et al., Journal of Organic Chemistry (1981), vol. 46(11) pp. 2273-2280.
Shi Shun et al., J. Org. Chem. vol. 68 (2003) pp. 6810-6813.
Lam et al., Bioorganic & Medicinal Chemistry Letters (2003) vol. 13(10) pp. 1795-1799.
Wang et al., Journal of Fluorine Chemistry, vol. 111(2) pp. 241-246 (2001).
Hamper et al., J. Agric. Food Chem. (1995), vol. 43, pp. 219-228.
Kumar, et al., Tetrahedron Letters, vol. 47, (2006), p. 1457-1460.
Burke, et al., Journal of Natural Products, 1986, vol. 49, pp. 522-523.
Hormi, Organic Syntheses, vol. 8, p. 247 (1993) & vol. 66, (1988), p. 173.
Andosova et al., Pharmaceutical Chemistry Journal (English Translation), vol. 12, No. 8, 1978, pp. 1019-1022.
Doyle, et al., Journal of the Chem. Society, 1963, pp. 5838-5845.
Anderson, et al., Journal of Organic Chem. vol. 51(6), 1986, pp. 945-947.

(Continued)

*Primary Examiner* — Patricia L Morris
(74) *Attorney, Agent, or Firm* — George W. Johnston; Patricia S. Rocha-Tramaloni; Kimberly J. Prior

(57) ABSTRACT

The present invention is concerned with isoxazole-pyridines of formula I, having affinity and selectivity for GABA A α5 receptor, their manufacture, pharmaceutical compositions containing them and their use as pharmaceuticals. The active compounds of the present invention are useful as cognitive enhancer or for the therapeutic and/or prophylactic treatment of cognitive disorders like Alzheimer's disease.

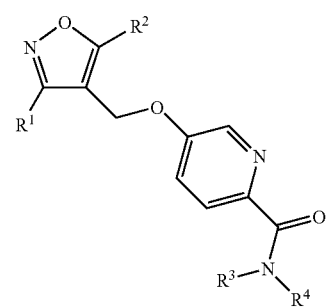

18 Claims, No Drawings

OTHER PUBLICATIONS

Bourbeau et al., Organic Letters, vol. 8(17), 2006, pp. 3679-3680.
Waldo et al., Org. Left. vol. (7) pp. 5203-5205 (2005).
Seydel et al., J. Med. Chem. vol. (19) pp. 483-492 (1976).
Kirk, K. L., J. Org. Chem. vol. (43) pp. 4381-4383 (1978).
Ley et al., Angew Chem, 2003 vol. 115 p. 5558-5606.
Hüttel et al., Liebigs, Ann. Chem. vol. 593, pp. 200-207 (1955) (English translation).
Austin et al., J. Org. Chem. vol. 46, pp. 2280-2286 (1981).
Schlosser et al., Eur. J. Org. Chem. vol. (24), p. 4181-4184 (2002).
Felix et al., J. Org. Chem. 1995, vol. 60 p. 3907-3909.
Otani et al., Neuroscience Letters, 2005, vol. 381 pp. 108-113.
Papadimitriou et al., Neuropsychobiology, 2001, vol. 43(3) pp. 141-144.
McCauley et al., American J. Med. Genetics, 2004, 131B, pp. 51-59.
Delong et al., Autism, 2007, vol. 11(2) pp. 135-147.
Solis Anez et al., Investigacion Clinica, 2007 vol. 28, pp. 529-541.
Fernandez et al., Nature, Neuroscience, 2007, vol. 10 pp. 411-413.
Rueda et al., Neuroscience Letters, 2008, vol. 433 pp. 22-27.
Cui et al., Cell. 2008, vol. 135, pp. 549-560.
Deshayes et al., Synthesis, 1984, pp. 868-870.

\* cited by examiner

PYRIDINES

PRIORITY TO RELATED APPLICATION(S)

This application claims the benefit of European Patent Application No. 09159457.2, filed May 5, 2009, which is hereby incorporated by reference in its entirety.

FIELD OF THE INVENTION

The present invention is concerned with isoxazole-pyridines having affinity and selectivity for GABA A α5 receptor, their manufacture, pharmaceutical compositions containing them and their use as pharmaceuticals.

BACKGROUND OF THE INVENTION

Receptors for the major inhibitory neurotransmitter, gamma-aminobutyric acid (GABA), are divided into two main classes: (1) GABA A receptors, which are members of the ligand-gated ion channel superfamily and (2) GABA B receptors, which are members of the G-protein linked receptor family. The GABA A receptor complex which is a membrane-bound heteropentameric protein polymer is composed principally of α, β and γ subunits.

Receptors for the major inhibitory neurotransmitter, gamma-aminobutyric acid (GABA), are divided into two main classes: (1) GABA A receptors, which are members of the ligand-gated ion channel superfamily and (2) GABA B receptors, which are members of the G-protein linked receptor family. The GABA A receptor complex which is a membrane-bound heteropentameric protein polymer is composed principally of α, β and γ subunits. Presently a total number of 21 subunits of the GABA A receptor have been cloned and sequenced. Three types of subunits (α, β and γ) are required for the construction of recombinant GABA A receptors which most closely mimic the biochemical, electrophysiological and pharmacological functions of native GABA A receptors obtained from mammalian brain cells. There is strong evidence that the benzodiazepine binding site lies between the α and γ subunits. Among the recombinant GABA A receptors, α1β2γ2 mimics many effects of the classical type-I BzR subtypes, whereas α2β2γ2, α3β2γ2 and α5β2γ2 ion channels are termed type-II BzR.

It has been shown by McNamara and Skelton in Psychobiology, 1993, 21:101-108 that the benzodiazepine receptor inverse agonist β-CCM enhance spatial learning in the Morris watermaze. However, β-CCM and other conventional benzodiazepine receptor inverse agonists are proconvulsant or convulsant which prevents their use as cognition enhancing agents in humans. In addition, these compounds are non-selective within the GABA A receptor subunits, whereas a GABA A α5 receptor partial or full inverse agonist which is relatively free of activity at GABA A a1 and/or α2 and/or α3 receptor can be used to provide a therapeutically active substance which is useful for enhancing cognition with reduced or without proconvulsant activity. It is also possible to use GABA A α5 inverse agonists which are not free of activity at GABA A α1 and/or α2 and/or α3 receptor but which are functionally selective for α5 containing subunits. However, inverse agonists which are selective for GABA A α5 subunits and are relatively free of activity at GABA A α1, α2 and α3 receptor are preferred.

Literature has been published to establish the link between GABA A α5 subunits and the therapeutic and/or prophylactic treatment of various diseases and disorders of the Central Nervous System, like Neuroscience Letts., 2005, 381, 108-13, Neuropsychobiology, 2001, 43(3), 141-44, Amer. J. Med. Genetics, 2004, 131B, 51-9, Autism 2007, 11(2): 135-47, Investigacion Clinica, 2007, 48, 529-41, Nature Neuroscience, 2007, 10, 411-13, Neuroscience Letts., 2008, 433, 22-7 and Cell 2008, 135, 549-60.

SUMMARY OF THE INVENTION

In particular, the present invention provides isoxazole-pyridines of formula I

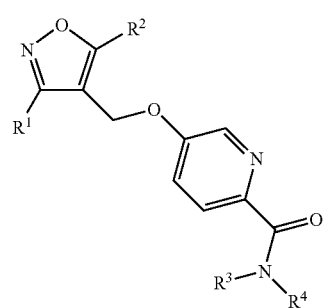

wherein
$R^1$ is selected from the group consisting of
  i) lower alkyl,
  ii) lower alkyl substituted by 1-5 substituents individually selected from amino, halogen, halogen-lower alkoxy, hydroxy, lower alkoxy, (lower alkyl,lower alkyl)N—, (lower alkyl,H)N—, nitro and lower alkyl-S(O)$_2$—,
  iii) aryl,
  iv) aryl substituted by 1-4 substituents individually selected from acetamidyl, acetyl, acetylamino, amido, amino, carboxy, cyano, halogen, halogen-lower alkoxy, halogen-lower alkyl, hydroxy, hydroxy-lower alkyl, lower alkoxy, lower alkoxy-lower alkyl, lower alkyl, (lower alkyl,lower alkyl)N—, (lower alkyl,H)N—, nitro and lower alkyl-S(O)$_2$—,
  v) heteroaryl, and
  vi) heteroaryl substituted by 1-4 substituents individually selected from acetamidyl, acetyl, acetylamino, amido, amino, carboxy, cyano, halogen, halogen-lower alkoxy, halogen-lower alkyl, hydroxy, hydroxy-lower alkyl, lower alkoxy, lower alkoxy-lower alkyl, lower alkyl, (lower alkyl,lower alkyl)N—, (lower alkyl,H)N—, nitro and lower alkyl-S(O)$_2$—;
$R^2$ is H, lower alkyl or lower alkyl substituted by 1-5 substituents individually selected from amino, halogen, halogen-lower alkoxy, hydroxy, lower alkoxy, (lower alkyl,lower alkyl)N—, (lower alkyl,H)N—, nitro and lower alkyl-S(O)$_2$—;
$R^3$ is H, lower alkyl or lower alkyl substituted by 1-5 substituents individually selected from amino, halogen, halogen-lower alkoxy, hydroxy, lower alkoxy, (lower alkyl,lower alkyl)N—, (lower alkyl,H)N—, nitro and lower alkyl-S(O)$_2$—;
$R^4$ is selected from the group consisting of
  i) H,
  ii) lower alkyl,
  iii) lower alkyl substituted by substituted by 1-5 substituents individually selected from amino, halogen, halogen-lower alkoxy, hydroxy, lower alkoxy, cycloalkyl, (lower alkyl,lower alkyl)N—, (lower alkyl,H)N—, nitro and lower alkyl-S(O)$_2$—, iv) heteroaryl,
v) heteroaryl substituted by 1-4 substituents individually selected from acetamidyl, acetyl, acetylamino, amido, amino, carboxy, cyano, halogen, halogen-lower alkoxy, halogen-lower alkyl, hydroxy, hydroxy-lower alkyl, lower alkoxy, lower alkoxy-lower alkyl, lower alkyl, (lower alkyl,lower alkyl)N—, (lower alkyl,H)N—, nitro and lower alkyl-S(O)$_2$—,
vi) cycloalkyl,
vii) cycloalkyl substituted by 1-4 substituents individually selected from acetamidyl, acetyl, acetylamino, amido, amino, carboxy, cyano, halogen, halogen-lower alkoxy, halogen-lower alkyl, hydroxy, hydroxy-lower alkyl, lower alkoxy, lower alkoxy-lower alkyl, lower alkyl, (lower alkyl,lower alkyl)N—, (lower alkyl,H)N—, nitro and lower alkyl-S(O)$_2$—,
viii) heterocyclyl,
ix) heterocyclyl substituted by 1-4 substituents individually selected from acetamidyl, acetyl, acetylamino, amido, amino, carboxy, cyano, halogen, halogen-lower alkoxy, halogen-lower alkyl, hydroxy, hydroxy-lower alkyl, lower alkoxy, lower alkoxy-lower alkyl, lower alkyl, (lower alkyl,lower alkyl)N—, (lower alkyl,H)N—, nitro and lower alkyl-S(O)$_2$—, and
x) —NR$^5$R$^6$;
or R$^3$ and R$^4$ together with the nitrogen to which they are attached form a heterocyclyl or a heterocyclyl substituted by 1-4 substituents individually selected from acetamidyl, acetyl, acetylamino, amido, amino, carboxy, cyano, halogen, halogen-lower alkoxy, halogen-lower alkyl, hydroxy, hydroxy-lower alkyl, lower alkoxy, lower alkoxy-lower alkyl, lower alkyl, —N(lower alkyl,lower alkyl), (lower alkyl,H)N—, nitro and lower alkyl-S(O)$_2$—;
R$^5$ is H or lower alkyl; and
R$^6$ is H or lower alkyl,
or a pharmaceutically acceptable salt or ester thereof.

DETAILED DESCRIPTION OF THE INVENTION

The present invention provides a compound of formula I and pharmaceutically acceptable salts and esters thereof, and pharmaceutical compositions containing them. The invention also provides methods for the manufacture of such compounds and compositions. The invention further provides methods for the therapeutic and/or prophylactic treatment of diseases and disorders related to the GABA A α5 receptor. The compounds of present invention are preferably inverse agonists of GABA A α5.

The compounds of present invention and their pharmaceutically acceptable salts and esters can be used, alone or in combination with other drugs, as cognitive enhancers or for the therapeutic and/or prophylactic treatment of acute neurological disorders, chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders.

The following definitions of the general terms used in the present description apply irrespective of whether the terms in question appear alone or in combination.

The term "lower alkyl", alone or in combination with other groups, stands for a hydrocarbon radical which can be linear or branched, with single or multiple branching, whereby the alkyl group in general comprises 1 to 6 carbon atoms, for example, methyl (Me), ethyl (Et), propyl, isopropyl (i-propyl), n-butyl, i-butyl (iso-butyl), 2-butyl (sec-butyl), t-butyl (tert-butyl) and the like. In particular, alkyl groups are groups with 1 to 4 carbon atoms, for example, methyl, ethyl, propyl, isopropyl and t-butyl.

The phrase "lower alkyl substituted by", alone or in combination with other groups, refers to lower alkyl as defined above, which is substituted by one or multiple substituents, preferably 1-5 substituents, individually selected from the group consisting of acetamidyl, acetyl, acetylamino, amido, amino, carboxy, cyano, cycloalkyl, halogen, halogen-lower alkoxy, heterocyclyl, hydroxy, lower alkoxy, (lower alkyl, lower alkyl)N—, (lower alkyl,H)N—, nitro, lower alkyl-S(O)$_2$— and the like. Preferred substituents are hydroxy, fluoro, methyl and cyclopropyl. Preferred substituted lower alkyl are hydroxy-lower alkyl, cyclopropyl-lower alkyl, cycloalkyl-lower alkyl, fluoro-lower alkyl and halogen-lower alkyl. Most preferred are 1-hydroxymethyl-propyl, 2,2,2-trifluoro-1-methyl-ethyl, 2,2,2-trifluoro-ethyl, 2-hydroxy-1,1-dimethyl-ethyl, 2-hydroxy-ethyl, cyclopropyl-methyl.

The term "halogen", alone or in combination with other groups, denotes chlorine (Cl), iodine (I), fluorine (F) and bromine (Br). Preferred halogen is fluorine.

The term "aryl", alone or in combination with other groups, refers to an aromatic carbocyclic group comprising 6 to 14, preferably 6 to 10, carbon atoms and having at least one aromatic ring or multiple condensed rings in which at least one ring is aromatic, for example phenyl (Ph), benzyl, naphthyl, biphenyl or indanyl. Preferred aryl group is phenyl.

The phrase "aryl substituted by", alone or in combination with other groups, refers to an aryl which is substituted by one or multiple substituents, preferably 1-4 substituents, whereby substitution at each ring atom individually is possible, with a substituent individually selected from the group consisting of amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl,lower alkyl)N—, (lower alkyl,H)N—, N(lower alkyl,lower alkyl)-lower alkyl, N(lower alkyl, H)-lower alkyl, nitro, lower alkyl-S(O)$_2$—, carboxy, carboxy-lower alkyl, lower alkyl-COO-lower alkyl, COO-lower alkyl, CO—N(lower alkyl,H)-lower alkyl, CO—N (lower alkyl,lower alkyl)-lower alkyl, CO—NH$_2$-lower alkyl, lower alkyl-CO— and the like. Preferred substituents are F and Cl. Preferred substituted aryl are halogen-aryl, halogen-phenyl, fluoro-phenyl and fluoro-aryl. Most preferred is 4-fluoro-phenyl.

The term "heteroaryl", alone or in combination with other groups, refers to an aromatic group having a single 4 to 8 membered ring or multiple condensed rings comprising 6 to 14, more preferably 6 to 10, ring atoms and containing 1, 2 or 3 heteroatoms, in which group at least one heterocyclic ring is aromatic. Examples of such groups include pyrrolyl, thienyl, furyl, pyrazolyl (pyrazyl), imidazolyl, triazolyl, tetrazolyl, thiazolyl, isothiazolyl, oxazolyl, isoxazolyl, pyridinyl, pyrimidinyl, pyrazinyl, pyridazinyl, indolyl, indazolyl, quinolinyl, isoquinolinyl, benzofuryl, benzothiazolyl, benzotriazolyl, benzoimidazolyl, benzooxazinyl, benzothiazinyl, benzothienyl and the like. Preferred heteroaryl groups are pyridinyl and pyrazolyl.

The phrase "heteroaryl substituted by", alone or in combination with other groups, refers to a heteroaryl which is substituted by one or multiple substituents, preferably 1-4 substituents, whereby substitution at each ring atom individually is possible, individually selected from the group consisting of amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl,lower alkyl)N—, (lower alkyl,H)N—, N(lower alkyl,lower alkyl)-lower alkyl, N(lower alkyl,H)-lower alkyl, nitro, lower alkyl-S(O)$_2$—, carboxy, carboxy-lower alkyl, lower alkyl-COO-lower alkyl, COO-lower alkyl, CO—N(lower alkyl,H)-lower alkyl, CO—N(lower alkyl,lower alkyl)-lower alkyl, CO—NH$_2$-lower alkyl, lower alkyl-CO— and the like. Preferred substituents are H, F and Me. Preferred "substituted heteroaryl" are lower alkyl-heteroaryl, lower alkyl-pyrazolyl, methyl-heteroaryl, methyl-pyrazolyl, halogen-heteroaryl, halogen-pyridinyl, fluoro-heteroaryl and fluoro-pyridinyl. Most preferred are 1-methyl-pyrazolyl and 5-fluoro-pyridin-2-yl.

The term "heterocyclyl", alone or in combination with other groups, refers to a 4 to 8 membered group containing 1, 2 or 3 ring heteroatoms individually selected from N, O and S. 1 or 2 ring heteroatoms are preferred. The "heterocyclyl" can be part of a bicyclic spiro ring. Preferred are 4 to 6 membered heterocyclyl, more preferred 5 to 6 membered heterocyclyl, each containing 1 or 2 ring heteroatoms selected from N, O and S. Examples of such "heterocyclyl" include pyrrolidinyl (pyrrolidinyl), tetrahydrofuryl, tetrahydrothienyl, tetrahydropyridyl (tetrahydropyridinyl), tetrahydropyryl, azetidyl (azetidinyl), thiazolidyl (thiazolidinyl), oxazolidyl (oxazolidinyl), piperidyl (piperidinyl), morpholinyl, thiomorpholinyl, piperazinyl, azepanyl, diazepanyl, oxazepanyl and the like. Preferred heterocyclyl groups are morpholinyl, thiomorpholinyl, 1,1-dioxo-thiomorpholinyl, tetrahydrofuryl, tetrahydropyryl, pyrrolidinyl and piperidinyl.

The phrase "heterocyclyl substituted by", alone or in combination with other groups, refer to a heterocyclyl, which is substituted by one or multiple substituents, preferably 1-4 substituents, whereby substitution at each ring atom individually is possible, with a substituent individually selected from the group consisting of amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl,lower alkyl)N—, (lower alkyl,H)N—, N(lower alkyl,lower alkyl)-lower alkyl, N(lower alkyl,H)-lower alkyl, nitro, lower alkyl-S(O)$_2$—, carboxy, carboxy-lower alkyl, lower alkyl-COO-lower alkyl, —COO-lower alkyl, CO—N(lower alkyl,H)-lower alkyl, CO—N(lower alkyl,lower alkyl)-lower alkyl, CO—NH$_2$-lower alkyl, lower alkyl-CO— and the like. Preferred substituents are hydroxyl, fluoro and methyl. Preferred substituted heterocyclyl are fluoro-heterocyclyl, halogen-heterocyclyl, fluoro-piperidinyl and halogen-piperidinyl. Most preferred is 4,4-difluoro-piperidyl.

The term "cycloalkyl", alone or in combination with other groups, refers to a 3 to 8 membered carbocyclic carbon ring, for example cyclopropyl, cyclobutyl, cyclopentyl, cyclohexyl, cycloheptyl or cyclooctyl. Preferred cycloalkyl are cyclopropyl, cyclobutyl and cyclopentyl.

The phrase "cycloalkyl substituted by", alone or in combination with other groups, refers to a cycloalkyl which is substituted by one or multiple substituents, preferably 1-4 substituents, whereby substitution at each ring atom individually is possible, with a substituent individually selected from the group consisting of halogen, halogen-lower alkoxy, halogen-lower alkyl, hydroxy, hydroxy-lower alkyl, lower alkoxy, lower alkoxy-lower alkyl, lower alkyl, (lower alkyl,lower alkyl)N—, (lower alkyl,H)N—, nitro, lower alkyl-S(O)$_2$— and the like.

The term "lower alkoxy", alone or in combination with other groups, stands for an "-G-lower alkyl" radical which can be linear or branched, with single or multiple branching, whereby the alkyl group in general comprises 1 to 6 carbon atoms, for example, methoxy (OMe, MeO), ethoxy (OEt), propoxy, isopropoxy (1-propoxy), n-butoxy, i-butoxy (iso-butoxy), 2-butoxy (sec-butoxy), t-butoxy (tert-butoxy), isopentyloxy (1-pentyloxy) and the like. Preferred alkoxy groups are groups with 1 to 4 carbon atoms.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable salts" refers to salts that are suitable for use in contact with the tissues of humans and animals without undue toxicity, irritation, allergic response, and the like. Examples of suitable salts with inorganic and organic acids are, but are not limited to, hydrochloric acid, nitric acid, sulfuric acid, phosphoric acid, sulphuric acid, citric acid, formic acid, fumaric acid, maleic acid, lactic acid, malic acid, acetic acid, succinic acid, tartaric acid, methane-sulfonic acid, p-toluenesulphonic acid, trifluoroacetic acid and the like.

The term "pharmaceutically acceptable esters" refers to a conventionally esterified compound having a carboxyl group. Examples of ester groups which are cleaved in vivo to the corresponding carboxylic acids are those in which the cleaved hydrogen is replaced with-lower alkyl which is optionally substituted with heterocyclyl, cycloalkyl, etc. Examples of substituted lower alkyl esters are those in which-lower alkyl is substituted with pyrrolidine, piperidine, morpholine, N-methylpiperazine, etc. Furthermore, the term "pharmaceutically acceptable esters" refers to a conventionally esterified compound having a hydroxy group. The hydroxy compounds can be converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which acids are non-toxic to living organisms.

The terms "pharmaceutically acceptable carrier" and "pharmaceutically acceptable auxiliary substance" refer to carriers and auxiliary substances such as diluents or excipients that are compatible with the other ingredients of the formulation and not deleterious to the recipient thereof.

"Therapeutically effective amount" means an amount that is effective to prevent, alleviate or ameliorate symptoms of disease or prolong the survival of the subject being treated.

The compounds of formula I can contain one or more asymmetric centres and can therefore occur as racemates, racemic mixtures, single enantiomers, diastereomeric mixtures and individual diastereomers. Additional asymmetric centres can be present depending upon the nature of the various substituents on the molecule. Each such asymmetric centre will independently produce two optical isomers and it is intended that all of the possible optical isomers and diastereomers in mixtures and as pure or partially purified compounds are included within this invention. The present invention is meant to comprehend all such isomeric forms of these compounds. The independent syntheses of these diastereomers or their chromatographic separations can be achieved as known in the art by appropriate modification of the methodology disclosed herein. Their absolute stereochemistry can be determined by the x-ray crystallography of crystalline products or crystalline intermediates which are derivatized, if necessary, with a reagent containing an asymmetric centre of known absolute configuration. If desired, racemic mixtures of the compounds can be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

Substituents at a double bond or a ring can be present in cis (=Z—) or trans (=E-) form, unless the stereochemistry is explicitly depicted in the corresponding compound formula I.

The term "pharmaceutical composition" encompasses a product comprising specified ingredients in pre-determined amounts or proportions, as well as any product that results, directly or indirectly, from combining specified ingredients in specified amounts. Preferably it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The following table lists abbreviations used within the present document.

TABLE 1

| abbreviations | |
|---|---|
| DCM | dichloromethane |
| DIPEA | N,N-diisopropylethylamin |
| DMF | N,N-dimethylformamide |
| EDAC | 3-(3-dimethylaminopropyl)-1-ethylcarbodiimide |
| h(s) | hour(s) |
| HCl | hydrochloride |
| HOBt | N-Hydroxybenzotriazole |
| LiOH, NaOH | lithium hydroxide, sodium hydroxide |
| Me$_3$Al | trimethylaluminium |
| MeOH, EtOH | methanol, ethanol |
| MS | mass spectrum |
| on | overnight |
| rt | room temperature |
| TBD | 1,5,7-triazabicyclo[4.4.0]dec-5-ene |
| TBTU | O-Benzotriazole-1-yl-N,N,N',N'-tetramethyluronium tetrafluoroborate |
| THF | tetrahydrofuran |

The invention also provides pharmaceutical compositions, methods of using, and methods of preparing the aforementioned compounds.

While the present invention has been described with reference to the specific embodiments thereof, it should be understood by those skilled in the art that various changes can be made and equivalents can be substituted without departing from the true spirit and scope of the invention. In addition, many modifications can be made to adapt a particular situation, material, composition of matter, process, process step or steps, to the objective spirit and scope of the present invention. All such modifications are intended to be within the scope of the claims appended hereto. All separate embodiments can be combined.

As described above, the novel compounds of the present invention and their pharmaceutically acceptable salts and esters possess valuable pharmacological properties and are ligands for GABA A α5 receptors. The compounds of the present invention can therefore be used, either alone or in combination with other drugs, for the treatment or prevention of disorders or diseases which are modulated by ligands for GABA A receptors containing the α5 subunit. These disorders or diseases include, but are not limited to acute neurological disorders, chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke, attentional disorders and need for cognition enhancement.

The invention therefore also relates to pharmaceutical compositions comprising a compound as defined herewithin and a pharmaceutically acceptable carrier and/or adjuvant.

The invention likewise embraces compounds as described above for use as therapeutically active substances, especially as therapeutically active substances for the treatment or prevention of disorders or diseases which are related to the GABA A α5 receptor, particularly for the treatment or prevention of acute neurological disorders, chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers.

In another preferred embodiment, the invention relates to a method for the treatment or prevention of disorders or diseases which are related to the GABA A α5 receptor, particularly for the treatment or prevention of acute neurological disorders, chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for cognition enhancement, which method comprises administering a compound as defined above to a human being or animal.

The invention also embraces the use of compounds as defined above for the treatment or prevention of disorders or diseases which are related to the GABA A α5 receptor, particularly for the treatment or prevention of acute neurological disorders, chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for cognition enhancement.

The invention also relates to the use of compounds as described above for the preparation of medicaments for the treatment or prevention of disorders or diseases which are related to the GABA A α5 receptor, particularly for the treatment or prevention of acute neurological disorders, chronic neurological disorders, cognitive disorders, Alzheimer's disease, memory deficits, schizophrenia, positive, negative and/ or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for the preparation of cognitive enhancers. Such medicaments comprise a compound as described above.

In particular, the invention provides the treatment or prevention of cognitive disorders, Alzheimer's disease, schizophrenia, positive, negative and/or cognitive symptoms associated with schizophrenia. Preferred is the treatment or prevention of Alzheimer's disease.

One embodiment of the invention is a compound of formula I,

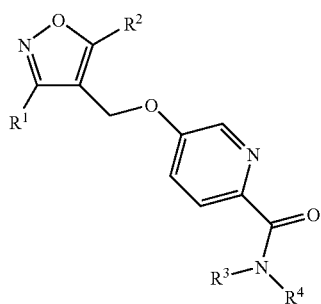

wherein
$R^1$ is selected from the group consisting of
i) lower alkyl,
ii) lower alkyl substituted by 1-5 substituents selected from amino, halogen, halogen-lower alkoxy, hydroxy, lower alkoxy, (lower alkyl,lower alkyl)N—, (lower alkyl,H)N—, nitro and lower alkyl-S(O)$_2$—,
iii) aryl,
iv) aryl substituted by 1-4 substituents selected from acetamidyl, acetyl, acetylamino, amido, amino, carboxy, cyano, halogen, halogen-lower alkoxy, halogen-lower alkyl, hydroxy, hydroxy-lower alkyl, lower alkoxy, lower alkoxy-lower alkyl, lower alkyl, (lower alkyl,lower alkyl)N—, (lower alkyl,H)N—, nitro and lower alkyl-S(O)$_2$—,
v) heteroaryl,
yl) heteroaryl substituted by 1-4 substituents selected from acetamidyl, acetyl, acetylamino, amido, amino, carboxy, cyano, halogen, halogen-lower alkoxy, halogen-lower alkyl, hydroxy, hydroxy-lower alkyl, lower alkoxy, lower alkoxy-lower alkyl, lower alkyl, (lower alkyl,lower alkyl)N—, (lower alkyl,H)N—, nitro and lower alkyl-S(O)$_2$—;
$R^2$ is H, lower alkyl or lower alkyl substituted by 1-5 substituents selected from amino, halogen, halogen-lower alkoxy, hydroxy, lower alkoxy, (lower alkyl,lower alkyl)N—, (lower alkyl,H)N—, nitro and lower alkyl-S(O)$_2$—;
$R^3$ is H, lower alkyl or lower alkyl substituted by 1-5 substituents selected from amino, halogen, halogen-lower alkoxy, hydroxy, lower alkoxy, (lower alkyl,lower alkyl)N—, (lower alkyl,H)N—, nitro and lower alkyl-S(O)$_2$—;
$R^4$ is selected from the group consisting of
i) H,
ii) lower alkyl,
iii) lower alkyl substituted by 1-5 substituents selected from amino, halogen, halogen-lower alkoxy, hydroxy, lower alkoxy, cycloalkyl, (lower alkyl,lower alkyl)N—, (lower alkyl,H)N—, nitro and lower alkyl-S(O)$_2$—,
iv) heteroaryl,
v) heteroaryl substituted by 1-4 substituents selected from acetamidyl, acetyl, acetylamino, amido, amino, carboxy, cyano, halogen, halogen-lower alkoxy, halogen-lower alkyl, hydroxy, hydroxy-lower alkyl, lower alkoxy, lower alkoxy-lower alkyl, lower alkyl, (lower alkyl,lower alkyl) N—, (lower alkyl,H)N—, nitro and lower alkyl-S(O)$_2$—,
vi) cycloalkyl,
vii) cycloalkyl substituted by 1-4 substituents selected from acetamidyl, acetyl, acetylamino, amido, amino, carboxy, cyano, halogen, halogen-lower alkoxy, halogen-lower alkyl, hydroxy, hydroxy-lower alkyl, lower alkoxy, lower alkoxy-lower alkyl, lower alkyl, (lower alkyl,lower alkyl) N—, (lower alkyl,H)N—, nitro and lower alkyl-S(O)$_2$—,
viii) heterocyclyl,
ix) heterocyclyl substituted by 1-4 substituents selected from acetamidyl, acetyl, acetylamino, amido, amino, carboxy, cyano, halogen, halogen-lower alkoxy, halogen-lower alkyl, hydroxy, hydroxy-lower alkyl, lower alkoxy, lower alkoxy-lower alkyl, lower alkyl, (lower alkyl,lower alkyl) N—, (lower alkyl,H)N—, nitro and lower alkyl-S(O)$_2$—, and
x) —NR$^5$R$^6$;
or $R^3$ and $R^4$ together with the nitrogen to which they are attached form a heterocyclyl or a heterocyclyl substituted by 1-4 substituents selected from acetamidyl, acetyl, acetylamino, amido, amino, carboxy, cyano, halogen, halogen-lower alkoxy, halogen-lower alkyl, hydroxy, hydroxy-lower alkyl, lower alkoxy, lower alkoxy-lower alkyl, lower alkyl, —N(lower alkyl,lower alkyl), (lower alkyl,H)N—, nitro and lower alkyl-S(O)$_2$—;
$R^5$ is H or lower alkyl; and
$R^6$ is H or lower alkyl,
or a pharmaceutically acceptable salt or ester thereof.

One certain embodiment of the invention are compounds, wherein $R^1$ is aryl, aryl substituted by 1-2 halogen atoms, heteroaryl or heteroaryl substituted by 1-2 halogen atoms.

One certain embodiment of the invention is a compound, wherein $R^1$ is aryl.

One certain embodiment of the invention is a compound, wherein $R^1$ is phenyl.

One certain embodiment of the invention is a compound, wherein $R^1$ is aryl substituted by 1-2 halogen atoms.

One certain embodiment of the invention is a compound, wherein $R^1$ is 4-fluoro-phenyl.

One certain embodiment of the invention is a compound, wherein $R^1$ is heteroaryl.

One certain embodiment of the invention is a compound, wherein $R^1$ is pyridinyl.

One certain embodiment of the invention is a compound, wherein $R^1$ is heteroaryl substituted by 1-2 halogen atoms.

One certain embodiment of the invention is a compound, wherein $R^1$ is 5-fluoro-pyridin-2-yl.

One certain embodiment of the invention is a compound, wherein $R^2$ is lower alkyl or lower alkyl substituted by 1-2 hydroxy groups.

One certain embodiment of the invention is a compound, wherein $R^2$ is lower alkyl.

One certain embodiment of the invention is a compound, wherein $R^2$ is methyl.

One certain embodiment of the invention is a compound, wherein $R^2$ is lower alkyl substituted by one or multiple hydroxy.

One certain embodiment of the invention is a compound, wherein $R^2$ is hydroxy-methyl.

One certain embodiment of the invention is a compound, wherein $R^3$ is H.

One certain embodiment of the invention is a compound, wherein $R^4$ is selected from the group consisting of
i) lower alkyl,
ii) lower alkyl substituted by 1-2 substituents selected from cycloalkyl, halogen, hydroxy and lower alkoxy,
iii) heteroaryl substituted by 1-2 lower alkyl groups,
iv) cycloalkyl,
v) cycloalkyl substituted by 1-2 hydroxy groups,
vi) heterocyclyl, and
vii) —$NR^5R^6$, wherein $R^5$ and $R^6$ are each independently selected from lower alkyl.

One certain embodiment of the invention is a compound, wherein $R^4$ is 1-hydroxymethyl-propyl, 1-methyl-pyrazyl, 2,2,2-trifluoro-1-methyl-ethyl, 2,2,2-trifluoro-ethyl, 2-hydroxy-1,1-dimethyl-ethyl, 2-hydroxy-cyclopentyl, 2-hydroxy-ethyl, cyclopropyl, cyclopropyl-methyl, ethyl, isopropyl, methyl, morpholinyl, —$N(CH_3)_2$, pyrrolidinyl, tert-butyl, tetrahydrofuranyl or tetrahydropyranyl.

One certain embodiment of the invention is a compound, wherein $R^4$ is selected from the group consisting of
i) lower alkyl,
ii) lower alkyl substituted by 1-2 substituents individually selected from halogen and hydroxy,
iii) heteroaryl substituted by 1-2 lower alkyl groups, and
iv) heterocyclyl.

One certain embodiment of the invention is a compound, wherein $R^4$ is 1-methyl-pyrazyl, 2,2,2-trifluoro-ethyl, 2-hydroxy-ethyl, isopropyl, morpholinyl or pyrrolidinyl.

One certain embodiment of the invention is a compound, wherein $R^4$ is lower alkyl.

One certain embodiment of the invention is a compound, wherein $R^4$ is methyl.

One certain embodiment of the invention is a compound, wherein $R^4$ is ethyl.

One certain embodiment of the invention is a compound, wherein $R^4$ is isopropyl.

One certain embodiment of the invention is a compound, wherein $R^4$ is tert-butyl.

One certain embodiment of the invention is a compound, wherein $R^4$ is lower alkyl substituted by 1-2 substituents selected from cycloalkyl, halogen, hydroxy and lower alkoxy.

One certain embodiment of the invention is a compound, wherein $R^4$ is 1-hydroxymethyl-propyl.

One certain embodiment of the invention is a compound, wherein $R^4$ is 2,2,2-trifluoro-1-methyl-ethyl.

One certain embodiment of the invention is a compound, wherein $R^4$ is 2,2,2-trifluoro-ethyl.

One certain embodiment of the invention is a compound, wherein $R^4$ is 2-hydroxy-1,1-dimethyl-ethyl.

One certain embodiment of the invention is a compound, wherein $R^4$ is 2-hydroxy-ethyl.

One certain embodiment of the invention is a compound, wherein $R^4$ is cyclopropyl-methyl.

One certain embodiment of the invention is a compound, wherein $R^4$ is heteroaryl substituted by 1-2 lower alkyl groups.

One certain embodiment of the invention is a compound, wherein $R^4$ is 1-methyl-pyrazyl.

One certain embodiment of the invention is a compound, wherein $R^4$ is cycloalkyl.

One certain embodiment of the invention is a compound, wherein $R^4$ is cyclopropyl.

One certain embodiment of the invention is a compound, wherein $R^4$ is cycloalkyl substituted by 1-2 hydroxy groups.

One certain embodiment of the invention is a compound, wherein $R^4$ is 2-hydroxy-cyclopentyl.

One certain embodiment of the invention is a compound, wherein $R^4$ is heterocyclyl.

One certain embodiment of the invention is a compound, wherein $R^4$ is morpholinyl.

One certain embodiment of the invention is a compound, wherein $R^4$ is pyrrolidinyl.

One certain embodiment of the invention is a compound, wherein $R^4$ is tetrahydrofuranyl.

One certain embodiment of the invention is a compound, wherein $R^4$ is tetrahydropyranyl.

One certain embodiment of the invention is a compound, wherein $R^4$ is —$NR^5R^6$, wherein $R^5$ and $R^6$ are each independently selected from lower alkyl.

One certain embodiment of the invention is a compound, wherein $R^4$ is —$N(CH_3)_2$.

One certain embodiment of the invention is a compound, wherein $R^3$ and $R^4$ together with the nitrogen atom to which they are attached form a heterocyclyl or a heterocyclyl substituted by 1-2 halogen atoms.

One certain embodiment of the invention is a compound, wherein $R^3$ and $R^4$ together with the nitrogen atom to which they are attached form 1,1-dioxo-thiomorpholinyl, 4,4-difluoro-piperidinyl or thiomorpholinyl.

One certain embodiment of the invention is a compound, wherein $R^3$ and $R^4$ together with the nitrogen atom to which they are attached from a heterocyclyl.

One certain embodiment of the invention is a compound, wherein $R^3$ and $R^4$ together with the nitrogen atom to which they are attached form a 1,1-dioxo-thiomorpholinyl.

One certain embodiment of the invention is a compound, wherein $R^3$ and $R^4$ together with the nitrogen atom to which they are attached form a thiomorpholinyl.

One certain embodiment of the invention is a compound, wherein $R^3$ and $R^4$ together with the nitrogen atom to which they are attached form a heterocyclyl substituted by 1-2 halogen atoms.

One certain embodiment of the invention is a compound, wherein $R^3$ and $R^4$ together with the nitrogen to which they are attached form a 4,4-difluoro-piperidinyl.

One certain embodiment of the invention is a compound selected from the group consisting of 5-(5-Methyl-3-phenyl-isoxazol-4-ylmethoxy)-pyridine-2-carboxylic acid (2-hydroxy-ethyl)-amide, 5-(5-Methyl-3-phenyl-isoxazol-4-ylmethoxy)-pyridine-2-carboxylic acid isopropylamide, 5-(5-Methyl-3-phenyl-isoxazol-4-ylmethoxy)-pyridine-2-carboxylic acid (tetrahydro-furan-3-yl)-amide, 5-(5-Methyl-3-phenyl-isoxazol-4-ylmethoxy)-pyridine-2-carboxylic acid N',N'-dimethyl-hydrazide, 5-(5-Methyl-3-phenyl-isoxazol-4-ylmethoxy)-pyridine-2-carboxylic acid morpholin-4-ylamide, 5-(5-Methyl-3-pyridin-2-yl-isoxazol-4-ylmethoxy)-pyridine-2-carboxylic acid (tetrahydro-pyran-4-yl)-amide, 5-(5-Methyl-3-pyridin-2-yl-isoxazol-4-ylmethoxy)-pyridine-2-carboxylic acid isopropylamide, 5-(5-Methyl-3-pyridin-2-yl-isoxazol-4-ylmethoxy)-pyridine-2-carboxylic acid (2-hydroxy-1,1-dimethyl-ethyl)-amide, 5-(5-Methyl-3-pyridin-2-yl-isoxazol-4-ylmethoxy)-pyridine-2-carboxylic acid morpholin-4-ylamide, (1,1-Dioxo-1,6-thiomorpholin-4-yl)-[5-(5-methyl-3-pyridin-2-yl-isoxazol-4-ylmethoxy)-pyridin-2-yl]-methanone, 5-(5-Methyl-3-pyridin-2-yl-isoxazol-4-ylmethoxy)-pyridine-2-carboxylic acid cyclopropylamide, 5-(5-Methyl-3-pyridin-2-yl-isoxazol-4-ylmethoxy)-pyridine-2-carboxylic acid cyclopropyl-methyl-amide, 5-(5-Methyl-3-pyridin-2-yl-isoxazol-4-ylmethoxy)-pyridine-2-carboxylic acid (2,2,2-trifluoro-ethyl)-amide, 5-(5-Methyl-3-pyridin-2-yl-isoxazol-4-ylmethoxy)-pyridine-2-carboxylic acid (2-hydroxy-ethyl)-amide, 5-(5-Methyl-3-pyridin-2-yl-isoxazol-4-ylmethoxy)-pyridine-2-carboxylic acid ethylamide, 5-(5-Methyl-3-pyridin-2-yl-isoxazol-4-ylmethoxy)-pyridine-2-carboxylic acid methylamide,

[5-(5-Methyl-3-pyridin-2-yl-isoxazol-4-ylmethoxy)-pyridin-2-yl]-thiomorpholin-4-yl-methanone, 5-(5-Methyl-3-pyridin-2-yl-isoxazol-4-ylmethoxy)-pyridine-2-carboxylic acid ((1S,2S)-2-hydroxy-cyclopentyl)-amide, 5-(5-Methyl-3-pyridin-2-yl-isoxazol-4-ylmethoxy)-pyridine-2-carboxylic acid (1-methyl-1H-pyrazol-4-yl)-amide, 5-(5-Methyl-3-pyridin-2-yl-isoxazol-4-ylmethoxy)-pyridine-2-carboxylic acid (1-hydroxymethyl-propyl)-amide, 5-(5-Methyl-3-pyridin-2-yl-isoxazol-4-ylmethoxy)-pyridine-2-carboxylic acid ((S)-1-hydroxy-methyl-propyl)-amide, 5-(5-Methyl-3-pyridin-2-yl-isoxazol-4-ylmethoxy)-pyridine-2-carboxylic acid ((S)-2,2,2-tri-fluoro-1-methyl-ethyl)-amide, 5-[3-(5-Fluoro-pyridin-2-yl)-5-methyl-isoxazol-4-ylmethoxy]-pyridine-2-carboxylic acid iso-propylamide, 5-[3-(5-Fluoro-pyridin-2-yl)-5-methyl-isoxazol-4-ylmethoxy]-pyridine-2-carboxylic acid (2-hydroxy-1,1-dimethyl-ethyl)-amide, 5-[3-(5-Fluoro-pyridin-2-yl)-5-methyl-isoxazol-4-ylmethoxy]-pyridine-2-carboxylic acid morpholin-4-ylamide, (1,1-Dioxo-1,6-thiomorpholin-4-yl)-{5-[3-(5-fluoro-pyridin-2-yl)-5-methyl-isoxazol-4-yl-methoxy]-pyridin-2-yl}-methanone, 5-[3-(5-Fluoro-pyridin-2-yl)-5-methyl-isoxazol-4-ylmethoxy]-pyridine-2-carboxylic acid cyclo-propylamide, 5-[3-(5-Fluoro-pyridin-2-yl)-5-methyl-isoxazol-4-ylmethoxy]-pyridine-2-carboxylic acid (2,2,2-trifluoro-ethyl)-amide, 5-[3-(4-Fluoro-phenyl)-5-hydroxymethyl-isoxazol-4-ylmethoxy]-pyridine-2-carboxylic acid isopropylamide, 5-[3-(4-Fluoro-phenyl)-5-hydroxymethyl-isoxazol-4-ylmethoxy]-pyridine-2-carboxylic acid (tetrahydro-pyran-4-yl)-amide, 5-[3-(4-Fluoro-phenyl)-5-hydroxymethyl-isoxazol-4-ylmethoxy]-pyridine-2-carboxylic acid cyclopropylamide, 5-[3-(4-Fluoro-phenyl)-5-hydroxymethyl-isoxazol-4-ylmethoxy]-pyridine-2-carboxylic acid (2,2,2-trifluoro-1-methyl-ethyl)-amide, 5-[3-(4-Fluoro-phenyl)-5-hydroxymethyl-isoxazol-4-ylmethoxy]-pyridine-2-carboxylic acid (2,2,2-trifluoro-ethyl)-amide, 5-[3-(4-Fluoro-phenyl)-5-hydroxymethyl-isoxazol-4-ylmethoxy]-pyridine-2-carboxylic acid ((S)-1-hydroxymethyl-propyl)-amide, 5-[3-(4-Fluoro-phenyl)-5-hydroxymethyl-isoxazol-4-ylmethoxy]-pyridine-2-carboxylic acid (1-methyl-1H-pyrazol-4-yl)-amide, 5-[3-(4-Fluoro-phenyl)-5-hydroxymethyl-isoxazol-4-ylmethoxy]-pyridine-2-carboxylic acid tert-butylamide, (4,4-Difluoro-piperidin-1-yl)-{5-[3-(4-fluoro-phenyl)-5-hydroxymethyl-isoxazol-4-ylmethoxy]-pyridin-2-yl}-methanone, 5-[3-(4-Fluoro-phenyl)-5-hydroxymethyl-isoxazol-4-ylmethoxy]-pyridine-2-carboxylic acid pyrrolidin-1-ylamide, and 5-[3-(4-Fluoro-phenyl)-5-hydroxymethyl-isoxazol-4-ylmethoxy]-pyridine-2-carboxylic acid morpholin-4-ylamide, or a pharmaceutically acceptable salt or ester thereof.

One certain embodiment of the invention is a compound selected from the group consisting of 5-(5-Methyl-3-phenyl-isoxazol-4-ylmethoxy)-pyridine-2-carboxylic acid (2-hydroxy-ethyl)-amide, 5-(5-Methyl-3-pyridin-2-yl-isoxazol-4-ylmethoxy)-pyridine-2-carboxylic acid isopropylamide, 5-(5-Methyl-3-pyridin-2-yl-isoxazol-4-ylmethoxy)-pyridine-2-carboxylic acid (2-hydroxy-ethyl)-amide, 5-(5-Methyl-3-pyridin-2-yl-isoxazol-4-ylmethoxy)-pyridine-2-carboxylic acid (1-methyl-1H-pyrazol-4-yl)-amide, 5-[3-(4-Fluoro-phenyl)-5-hydroxymethyl-isoxazol-4-ylmethoxy]-pyridine-2-carboxylic acid (2,2,2-trifluoro-ethyl)-amide, 5-[3-(4-Fluoro-phenyl)-5-hydroxymethyl-isoxazol-4-ylmethoxy]-pyridine-2-carboxylic acid (1-methyl-1H-pyrazol-4-yl)-amide, 5-[3-(4-Fluoro-phenyl)-5-hydroxymethyl-isoxazol-4-ylmethoxy]-pyridine-2-carboxylic acid pyrrolidin-1-ylamide, and 5-[3-(4-Fluoro-phenyl)-5-hydroxymethyl-isoxazol-4-ylmethoxy]-pyridine-2-carboxylic acid morpholin-4-ylamide, or a pharmaceutically acceptable salt or ester thereof.

One certain embodiment of the invention is a compound selected from the group consisting of 5-(5-Methyl-3-pyridin-2-yl-isoxazol-4-ylmethoxy)-pyridine-2-carboxylic acid isopropylamide, 5-[3-(4-Fluoro-phenyl)-5-hydroxymethyl-isoxazol-4-yl-methoxy]-pyridine-2-carboxylic acid (1-methyl-1H-pyrazol-4-yl)-amide, 5-[3-(4-Fluoro-phenyl)-5-hydroxymethyl-isoxazol-4-yl-methoxy]-pyridine-2-carboxylic acid pyrrolidin-1-ylamide, and 5-[3-(4-Fluoro-phenyl)-5-hydroxymethyl-isoxazol-4-yl-methoxy]-pyridine-2-carboxylic acid morpholin-4-ylamide, or a pharmaceutically acceptable salt or ester thereof.

One certain embodiment of the invention is 5-(5-Methyl-3-pyridin-2-yl-isoxazol-4-ylmethoxy)-pyridine-2-carboxylic acid isopropylamide.

One certain embodiment of the invention is 5-[3-(4-Fluoro-phenyl)-5-hydroxymethyl-isoxazol-4-ylmethoxy]-pyridine-2-carboxylic acid (1-methyl-1H-pyrazol-4-yl)-amide.

One certain embodiment of the invention is 5-[3-(4-Fluoro-phenyl)-5-hydroxymethyl-isoxazol-4-ylmethoxy]-pyridine-2-carboxylic acid pyrrolidin-1-ylamide.

One certain embodiment of the invention is 5-[3-(4-Fluoro-phenyl)-5-hydroxymethyl-isoxazol-4-ylmethoxy]-pyridine-2-carboxylic acid morpholin-4-ylamide.

One certain embodiment of the invention is a process for preparing a compound of formula I as defined herewithin, which process comprises reacting a compound of formula $R^3R^4NH$ (II) with a compound of formula III,

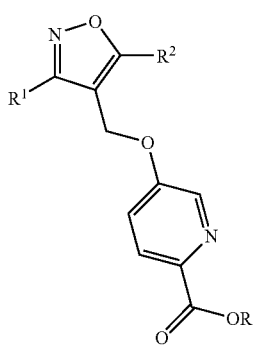

wherein any residues and variables have any of the meanings as defined herewithin and R is lower alkyl or H, under standard reaction conditions such as TBTU and Hüning's Base in DMF.

One certain embodiment of the invention is a compound as described herewithin, whenever prepared by a process as defined above.

One certain embodiment of the invention is a compound as described herewithin for the use as a pharmaceutical.

One certain embodiment of the invention is a compound as described herewithin for the use as a therapeutically active substance.

One certain embodiment of the invention is a compound as described herewithin for the use for the therapeutic and/or prophylactic treatment of a disorder or condition mediated by the GABA A α5 receptor, or that can be treated via modulation of the GABA A α5 receptor.

One certain embodiment of the invention is a compound as described herewithin for the use for the therapeutic and/or prophylactic treatment of diseases and disorders which are related to the GABA A α5 receptor.

One certain embodiment of the invention is a compound as described herewithin for the use for the therapeutic and/or prophylactic treatment of acute neurological disorders, chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers.

One certain embodiment of the invention is a medicament, comprising a compound as described herewithin.

One certain embodiment of the invention is a pharmaceutical composition comprising a compound as described herewithin as an active ingredient and a pharmaceutically acceptable carrier and/or a pharmaceutically acceptable auxiliary substance.

One certain embodiment of the invention is a pharmaceutical composition, comprising a compound as described herewithin for the therapeutic and/or prophylactic treatment of a disorder or condition mediated by the GABA A α5 receptor, or that can be treated via modulation of the GABA A α5 receptor.

One certain embodiment of the invention is a pharmaceutical composition, comprising a compound as described herewithin for the therapeutic and/or prophylactic treatment of diseases and disorders which are related to the GABA A α5 receptor.

One certain embodiment of the invention is a pharmaceutical composition, comprising a compound as described herewithin for the therapeutic and/or prophylactic treatment of acute neurological disorders, chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers.

One certain embodiment of the invention is the use of a compound as described herewithin for the manufacture of a medicament for the therapeutic and/or prophylactic treatment of a disorder or condition mediated by the GABA A α5 receptor, or that can be treated via modulation of the GABA A α5 receptor.

One certain embodiment of the invention is the use of a compound as described herewithin for the manufacture of a medicament for the therapeutic and/or prophylactic treatment of diseases and disorders which are related to the GABA A α5 receptor.

One certain embodiment of the invention is the use of a compound as described herewithin for the manufacture of a medicament for the therapeutic and/or prophylactic treatment of acute neurological disorders, chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers.

One certain embodiment of the invention is the use of a compound as described herewithin for the therapeutic and/or prophylactic treatment of a disorder or condition mediated by the GABA A α5 receptor, or that can be treated via modulation of the GABA A α5 receptor.

One certain embodiment of the invention is the use of a compound as described herewithin for the therapeutic and/or prophylactic treatment of diseases and disorders which are related to the GABA A α5 receptor.

One certain embodiment of the invention is the use of a compound as described herewithin for the therapeutic and/or prophylactic treatment of acute neurological disorders, chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers.

One certain embodiment of the invention is a method for the therapeutic and/or prophylactic treatment of a disorder or condition mediated by the GABA A α5 receptor, or that can be treated via modulation of the GABA A α5 receptor, particularly for the therapeutic and/or prophylactic treatment of acute neurological disorders, chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers, which method comprises administering a compound as described herewithin to a human being or animal.

One certain embodiment of the invention is a method for the therapeutic and/or prophylactic treatment of diseases and disorders which are related to the GABA A α5 receptor, particularly for the therapeutic and/or prophylactic treatment of acute neurological disorders, chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers, which method comprises administering a compound as described herewithin to a human being or animal.

The compounds of formula I can be prepared in accordance with the following schemes. The starting material is commercially available or can be prepared in accordance with known methods. Any previously defined residues and variables will continue to have the previously defined meaning unless otherwise indicated.

Reaction Schemes

The present compounds of formula I and their pharmaceutically acceptable salts can be prepared by a process comprising the steps of:

A) Reacting a compound of formula 1 with hydroxylamine hydrochloride in a suitable solvent, such as ethanol and water in the presence of a base, such as aqueous sodium hydroxide to give a compound of formula 2, followed by reacting the compound of formula 2 with a chlorinating agent such as N-chlorosuccinimide in a suitable solvent, such as DMF to give a compound of formula 3.

Scheme 1: Synthesis of intermediates 3

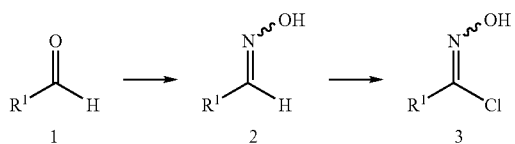

B) A compound of formula 3 is then reacted further to a compound of formula 6 by reacting
  i) with a compound of formula 4 in the presence of a suitable base, such as triethylamine, in a suitable solvent, such as chloroform, or
  ii) with a compound of formula 5 in the presence of a suitable base, such as triethylamine, in a suitable solvent, such as diethylether.

Scheme 2: Synthesis of intermediates 6

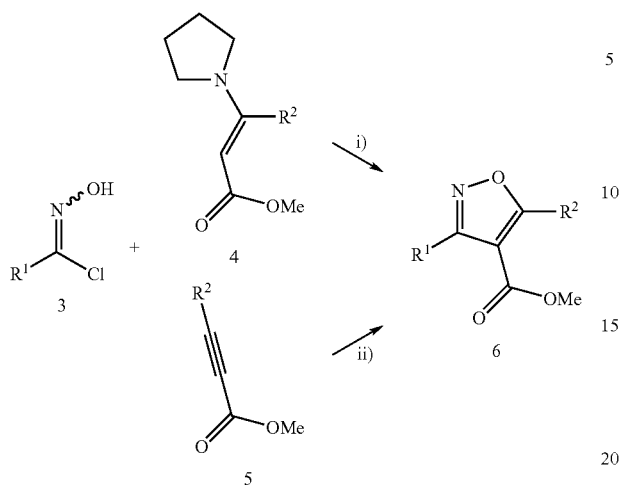

C) A compound of formula 6 is then reacted to a compound of formula 8 with
  i) a reducing agent, such as lithium aluminum hydride, in a suitable solvent, such as THF to give a compound of formula 8, or
  ii-1) a hydrolytic agent such as NaOH or LiOH in a suitable solvent such as THF, MeOH or EtOH, water to give a compound of formula 7,
  ii-2) followed by reacting a compound of formula 7 with a reducing agent, such as lithium aluminium hydride or ethylchloroformate in the presence of sodiumborohydride in a suitable solvent such as THF or water.

Scheme 3: Synthesis of intermediates 8

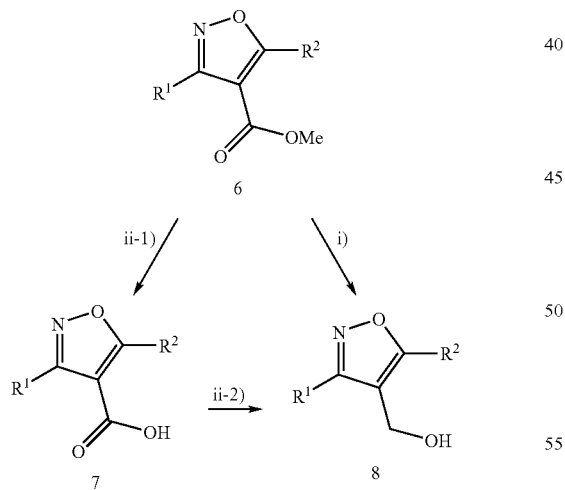

D-1) A compound of formula 9 can be formed by reacting the compound of formula 6 with benzaldehyde in the presence of a base such as sodium ethoxide in suitable solvent such as ethanol under reflux, followed by reacting a compound of formula 9 with a reducing agent, such as lithiumaluminiumhydride or ethylchloroformate in the presence of sodiumborohydride and a suitable base such as triethylamine in a suitable solvent such as THF or water to give a compound of formula 10. A compound of formula 10 can then be treated with triphenylphosphine and diethylazodicarboxylate, in a suitable solvent, such as THF, with an appropriate phenol such as 5-hydroxy-pyridine-2-carboxylic acid ethyl ester to give a compound of formula 11 followed by reacting a compound of formula 11 with an oxidizing agent such as Osmium(VIII)-oxide and sodium metaperiodate in the presence of benzyltriethylammonium chloride in the presence of a suitable solvent such as, dioxane and water using microwave heating to give a compound of formula 12: followed by reacting a compound of formula 12 with a reducing agent, such as sodiumborohydride in a suitable solvent such as methanol to give a compound of formula 13.

Scheme 4: Synthesis of intermediates 9, 10, 11, 12 and 13

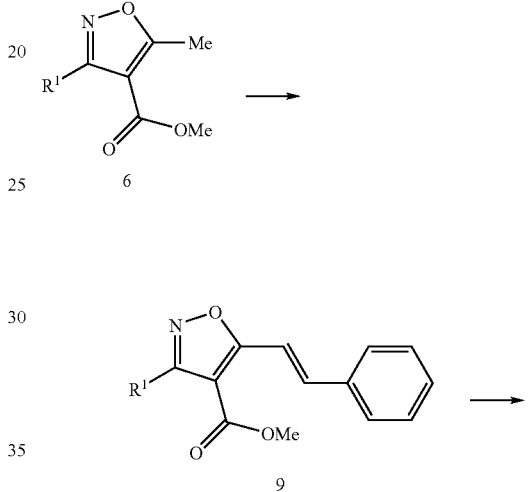

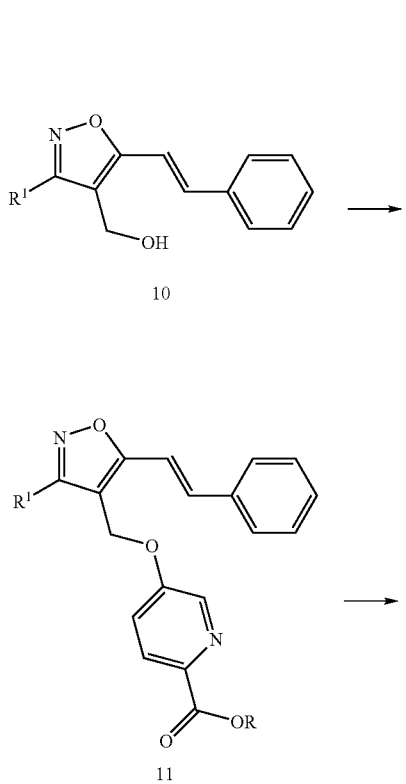

D-2) A compound of formula 8 can be treated with triphenylphosphine and diethylazodicarboxylate, in a suitable solvent, such as THF, with an appropriate phenol such as 5-hydroxy-pyridine-2-carboxylic acid ethyl ester to give a compound of formula 14.

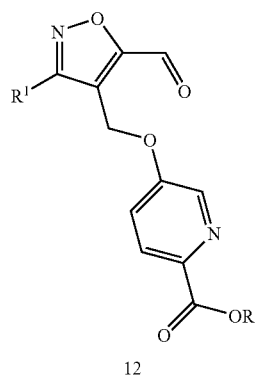

12

Scheme 5: Synthesis of intermediates III

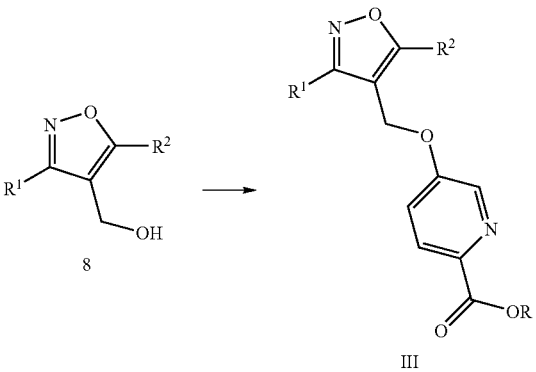

N) Compounds of formula 13 and formula III can further react according to standard methods to give compounds of formula I.

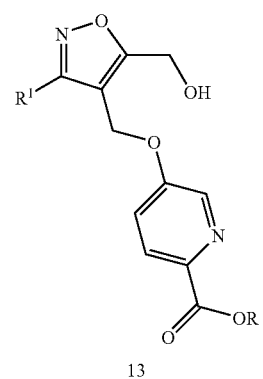

13

Scheme 6: Synthesis of compounds of formula I

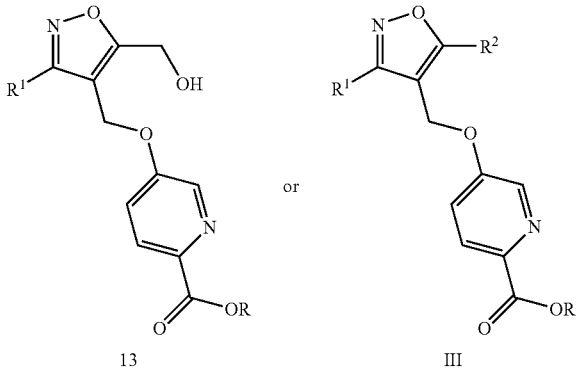

13 or III

-continued

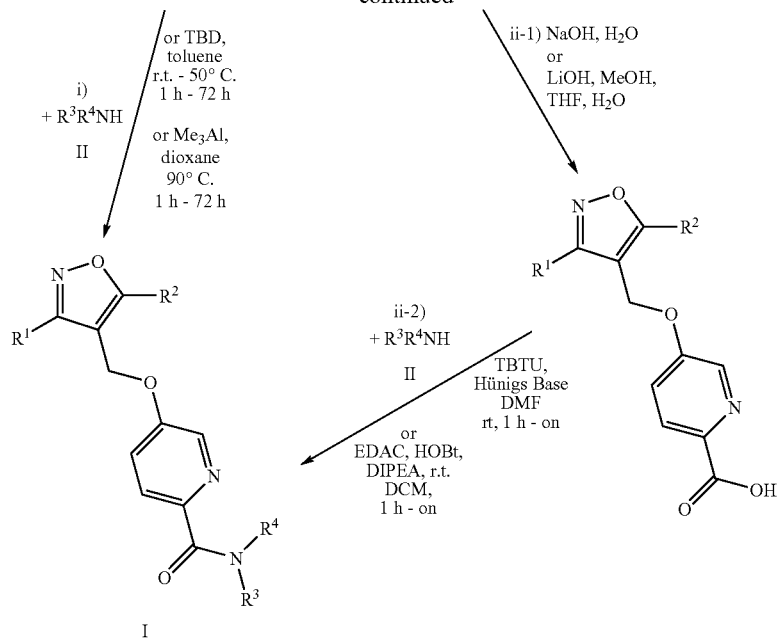

The corresponding pharmaceutically acceptable salts with acids can be obtained by standard methods known to the person skilled in the art, e.g. by dissolving the compound of formula I in a suitable solvent such as e.g. dioxan or THF and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilization.

The conversion into pharmaceutically acceptable esters of compounds of formula I bearing a carboxy group can be carried out e.g. by treatment of a suitable carboxy group with a suitable alcohol using e.g. a condensating reagent such as benzotriazol-1-yloxytris(dimethylamino)-phosphonium hexafluorophosphate (BOP), N,N-dicylohexyl-carbodiimide (DCC), N-(3-dimethylaminopropyl)-N'-ethylcarbodiimide hydrochloride (EDCI) or O-(1,2-dihydro-2-oxo-1-pyridyl)-N,N,N,N-tetra-methyluronium-tetrafluoro-borate (TPTU), or by direct reaction with a suitable alcohol under acidic conditions, as for example in the presence of a strong mineral acid like hydrochloric acid, sulfuric acid and the like. The conversion into pharmaceutically acceptable esters of compounds of formula I bearing a hydroxy group can be carried out with suitable acids by analogous methods.

Insofar as their preparation is not described in the examples, the compounds of formula I as well as all intermediate products can be prepared according to analogous methods or according to the methods set forth herewithin. Starting materials are commercially available, known in the art or can be prepared by methods known in the art or in analogy thereto.

It will be appreciated that the compounds of formula I in this invention can be derivatized at functional groups to provide derivatives which are capable of conversion back to the parent compound in vivo.

Pharmacological Tests

The compounds of formula I and their pharmaceutically acceptable salts and esters possess valuable pharmacological properties. Compounds of the present invention are ligands for GABA A receptors containing the α5 subunit and are therefore useful in the therapy where cognition enhancement is required.

The compounds were investigated in accordance with the test given hereinafter:

Membrane Preparation and Binding Assay

The affinity of compounds at GABA A receptor subtypes was measured by competition for [$^3$H]flumazenil (85 Ci/mmol; Roche) binding to HEK293 cells expressing rat (stably transfected) or human (transiently transfected) receptors of composition α1β3γ2, α2β3γ2, α3β3γ2 and α5β3γ2.

Cell pellets were suspended in Krebs-tris buffer (4.8 mM KCl, 1.2 mM $CaCl_2$, 1.2 mM $MgCl_2$, 120 mM NaCl, 15 mM Tris; pH 7.5; binding assay buffer), homogenized by polytron for ca. 20 sec on ice and centrifuged for 60 min at 4° C. (50000 g; Sorvall, rotor: SM24=20000 rpm). The cell pellets were re-suspended in Krebs-tris buffer and homogenized by polytron for ca. 15 sec on ice. Protein was measured (Bradford method, Bio-Rad) and aliquots of 1 mL were prepared and stored at −80° C.

Radioligand binding assays were carried out in a volume of 200 mL (96-well plates) which contained 100 mL of cell membranes, [$^3$H]flumazenil at a concentration of 1 nM for α1, α2 and α3 subunits and 0.5 nM for α5 subunits and the test compound in the range of $10\text{-}10^{-3} \times 10^{-6}$ M. Nonspecific binding was defined by $10^{-5}$ M diazepam and typically represented less than 5% of the total binding. Assays were incubated to equilibrium for 1 hour at 4° C. and harvested onto GF/C uni-filters (Packard) by filtration using a Packard harvester and washing with ice-cold wash buffer (50 mM Tris; pH 7.5). After drying, filter-retained radioactivity was detected by liquid scintillation counting. Ki values were calculated using Excel-Fit (Microsoft) and are the means of two determinations.

The compounds of the accompanying examples were tested in the above described assay, and the preferred compounds were found to possess a Ki value for displacement of [$^3$H]flumazenil from α5 subunits of the rat GABA A receptor of 100 nM or less. Most preferred are compounds with a Ki (nM)<35. In a preferred embodiment the compounds of the invention are binding selective for the α5 subunit relative to the α1, α2 and α3 subunit. Representative test results are listed below.

TABLE 2 human Ki (hKi) values

| Ex. | hKi GABA A α5 (nM) |
|---|---|
| 1 | 15.4 |
| 2 | 8.9 |
| 3 | 13.9 |
| 4 | 26.5 |
| 5 | 17 |
| 6 | 4.8 |
| 7 | 3.2 |
| 8 | 22.3 |
| 9 | 4.4 |
| 10 | 34.2 |
| 11 | 3.5 |
| 12 | 7.1 |
| 13 | 4.6 |
| 14 | 7.8 |
| 15 | 5.8 |
| 16 | 7.1 |
| 17 | 32.9 |
| 18 | 5.6 |
| 19 | 1.7 |
| 20 | 8.1 |
| 21 | 4.3 |
| 22 | 5.6 |
| 23 | 3.3 |
| 24 | 17.5 |
| 25 | 3.9 |
| 26 | 36.9 |
| 27 | 2.6 |
| 28 | 4.2 |
| 29 | 70.2 |
| 30 | 30.3 |
| 31 | 23.3 |
| 32 | 60.4 |
| 33 | 10.2 |
| 34 | 8.3 |
| 35 | 3.4 |
| 36 | 74.2 |
| 37 | 10.2 |
| 38 | 3.4 |
| 39 | 0.8 |
| 40 | 23.3 |

Pharmaceutical Compositions

The invention also provides pharmaceutical compositions containing compounds of formula I as well as their pharmaceutically acceptable salts and esters and a pharmaceutically acceptable carrier. The pharmaceutical compositions of the invention can be formulated for any route of administration, such as oral, sub-lingual, buccal, parenteral (subcutaneous, intramuscular, intravenous), rectal, topical, intranasal and trough inhalation or insufflation, and comprise at least one compound of formula I or pharmaceutically acceptable salts or esters thereof, with any pharmaceutically suitable ingredient, excipient, carrier, adjuvant or vehicle. Oral pharmaceutical compositions are e.g. tablets, coated tablets, dragées, hard gelatine capsules, soft gelatin capsules, solutions, emulsions or suspensions. Rectal pharmaceutical compositions are e.g. in the form of suppositories.

The compounds of formula I and their pharmaceutically disorders or diseases salts and esters can be processed with pharmaceutically inert, inorganic or organic excipients for the production of tablets, coated tablets, dragées and hard gelatin capsules. Examples are lactose, corn starch or derivatives thereof, talc, stearic acid or its salts etc can be used as such excipients e.g. for tablets, dragées and hard gelatin capsules. Suitable excipients for soft gelatin capsules are e.g. vegetable oils, waxes, fats, semisolid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

The pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of formula I or of the corresponding amount of a pharmaceutically acceptable salt or ester thereof. The daily dosage can be administered as single dose or in divided doses and, in addition, the upper limit can also be exceeded when necessary.

Examples of compositions according to the invention are, but are not limited to:

EXAMPLE A

Tablets of the following composition are manufactured in the usual manner:

TABLE 3 possible tablet composition

| ingredient | Mg/tablet |
|---|---|
| Compound of formula I | 5 |
| Lactose | 45 |
| Corn starch | 15 |
| Microcrystalline cellulose | 34 |
| Magnesium stearate | 1 |
| Tablet weight | 100 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

EXAMPLE B

Capsules of the following composition are manufactured:

TABLE 4

| possible capsule composition | |
|---|---|
| ingredient | mg/capsule |
| Compound of formula I | 10 |
| Lactose | 155 |
| Corn starch | 30 |
| Talc | 5 |
| Capsule fill weight | 200 |

Manufacturing Procedure
1. Mix items 1, 2 and 3 in a suitable mixer for 30 minutes.
2. Add item 4 and mix for 3 minutes.
3. Fill into a suitable capsule.

Items 1, 2 and 3 are firstly mixed in a mixer and then in a comminuting machine. The mixture is returned to the mixer, item 4 is added thereto and mixed thoroughly. The mixture is filled by machine into hard gelatine capsules.

EXAMPLE C

Suppositories of the following composition are manufactured:

TABLE 5

| possible suppository composition | |
|---|---|
| ingredient | mg/supp. |
| Compound of formula I | 15 |
| Suppository mass | 1285 |
| Total | 1300 |

Manufacturing Procedure

Item 2 is melted in a glass or steel vessel, mixed thoroughly and cooled to 45° C. Thereupon, the finely powdered item 1 is added thereto and stirred until it has dispersed completely. The mixture is poured into suppository moulds of suitable size, left to cool, the suppositories are then removed from the moulds and packed individually in wax paper or metal foil.

EXPERIMENTAL PART

The following examples 1-39 are provided for illustration of the invention. They should not be considered as limiting the scope of the invention, but merely as being representative thereof.

EXAMPLE 1

5-(5-Methyl-3-phenyl-isoxazol-4-ylmethoxy)-pyridine-2-carboxylic acid (2-hydroxy-ethyl)-amide

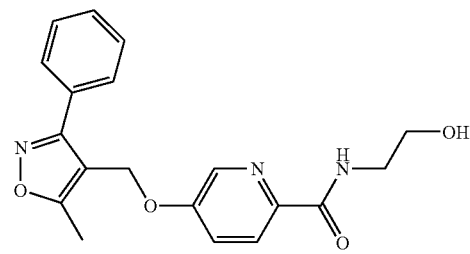 [SMILES: Cc1onc(-c2ccccc2)c1COc1ccc(C(=O)NCCO)nc1]

a) 5-Hydroxy-pyridine-2-carboxylic acid ethyl ester

To a stirred solution of 5-hydroxy-pyridine-2-carboxylic acid (1.25 g, 9.0 mmol) in ethanol (40 mL) was added concentrated sulfuric acid (3 mL, 56.3 mmol) and the resulting solution heated at reflux under an atmosphere of argon for 20 h. The solution was then cooled to 0° C. then sodium hydroxide (2 N, 55 mL) was added. Saturated aqueous sodium bicarbonate and 10% w/w citric acid solution were then added to bring the pH to 7 and the resulting solution concentrated to ~70 mL). The resulting mixture was extracted with ethyl acetate (3×50 mL) and the combined organic extracts dried, filtered and concentrated to afford the title compound (829 mg, 55%) as an off white solid. MS: m/e=168.3 [M+H]$^+$.

b) 5-(5-Methyl-3-phenyl-isoxazol-4-ylmethoxy)-pyridine-2-carboxylic acid ethyl ester To a stirred solution of (5-methyl-3-phenyl-4-isoxazolyl)methanol (570 mg, 3.01 mmol) and 5-hydroxy-pyridine-2-carboxylic acid ethyl ester (655 mg, 3.92 mmol) in THF (15 mL) under argon was added triphenylphosphine (1.03 g, 3.93 mmol). Diethyl azodicarboxylate (1.71 mL of a 40% solution in toluene, 682 mg, 3.92 mmol) was added dropwise. After 20 h the reaction mixture was concentrated in vacuo, water was added, and the reaction mixture extracted with ethyl acetate. The combined organic extracts were dried, filtered and concentrated then purified by chromatography (silica, 10 to 60% ethyl actetate in heptane) afforded the title compound (440 mg, 43%) as a pink oil. MS: m/e=339.3 [M+H]$^+$.

c) 5-(5-Methyl-3-phenyl-isoxazol-4-ylmethoxy)-pyridine-2-carboxylic acid (2-hydroxy-ethyl)-amide To a stirred solution of 5-(5-methyl-3-phenyl-isoxazol-4-ylmethoxy)-pyridine-2-carboxylic acid ethyl ester (140 mg, 0.41 mmol) in toluene (1 mL) was added ethanolamine (30 mg, 0.49 mmol) and 1,5,7-triazabicyclo[4.4.0]dec-5-ene (35 mg, 0.25 mmol) and the reaction stirred under argon for 6 h. Seignette salt solution (4 mL) was added and the solution extracted with ethyl acetate (3×20 mL), dried, filtered, and concentrated in vacuo. Purification by chromatography (silica, 0 to 10% methanol in dichloromethane) afforded the title compound (128 mg, 88%) as a light yellow gum. MS: m/e=354.3 [M+H]$^+$.

EXAMPLE 2

5-(5-Methyl-3-phenyl-isoxazol-4-ylmethoxy)-pyridine-2-carboxylic acid isopropylamide

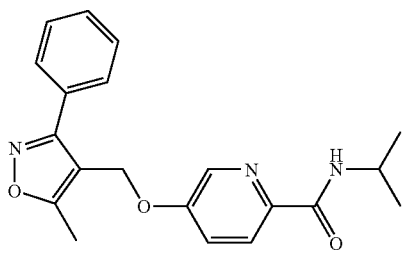 [SMILES: Cc1onc(-c2ccccc2)c1COc1ccc(C(=O)NC(C)C)nc1]

To a stirred solution of isopropylamine (98 mg, 1.66 mmol) in dioxane (3 mL) was added dropwise a trimethylaluminium (0.83 mL, 2 M solution in toluene, 1.66 mmol) and the resulting solution stirred under argon for 30 min. A solution of 5-(5-methyl-3-phenyl-isoxazol-4-ylmethoxy)-pyridine-2-carboxylic acid ethyl ester (140 mg, 0.41 mmol) in dioxane (3 mL) was then added and the resulting solution stirred under argon for a further 20 h at 85° C. The reaction mixture was cooled and Seignette salt solution (2 mL) and water (2 mL) were added. The reaction mixture was extracted with ethyl acetate (3×20 mL). The combined organic layers were dried, filtered and concentrated in vacuo. Purification by chromatography (silica, 0 to 6% methanol in dichloromethane) gave the title compound (138 mg, 95%) as a light yellow solid. MS: m/e=352.3 [M+H]$^+$.

EXAMPLE 3

Rac-5-(5-Methyl-3-phenyl-isoxazol-4-ylmethoxy)-pyridine-2-carboxylic acid (tetrahydro-furan-3-yl)-amide

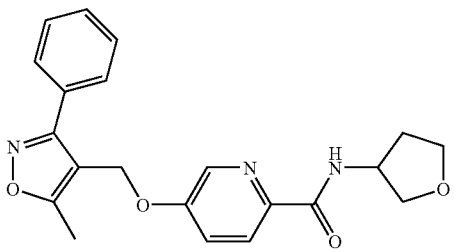 [SMILES: Cc1onc(-c2ccccc2)c1COc1ccc(C(=O)NC2CCOC2)nc1]

As described for example 2, 5-(5-methyl-3-phenyl-isoxazol-4-ylmethoxy)-pyridine-2-carboxylic acid ethyl ester (140 mg, 0.41 mmol) was converted, using rac-3-aminotetrahydrofuran instead of isopropylamine, to the title compound (114 mg, 73%) which was obtained as a light yellow solid after purification by chromatography (silica, 0 to 6% methanol in dichloromethane). MS: m/e=380.3 [M+H]$^+$.

EXAMPLE 4

5-(5-Methyl-3-phenyl-isoxazol-4-ylmethoxy)-pyridine-2-carboxylic acid N',N'-dimethyl-hydrazide

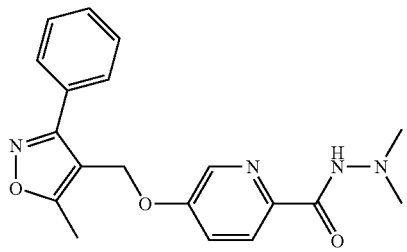 [SMILES: Cc1onc(-c2ccccc2)c1COc1ccc(C(=O)NN(C)C)nc1]

a) 5-(5-Methyl-3-phenyl-isoxazol-4-ylmethoxy)-pyridine-2-carboxylic acid ethyl ester To a solution of (5-methyl-3-phenyl-isoxazol-4-yl)-methanol (870 mg, 4.6 mmol) in THF (30 mL) was added 5-hydroxy-pyridine-2-carboxylic acid ethyl ester (999 mg, 6.0 mmol) and triphenylphosphine (1.57 g, 6.0 mmol) at ambient temperature under an argon atmosphere. Then diethyl azodicarboxylate (2.74 mL, 40% solution in toluene, 6.0 mmol) was added and the reaction mixture was stirred for 24 h at room temperature. The reaction mixture was evaporated and then diluted with water (40 mL) and extracted with ethyl acetate (3×50 mL). The combined organic layers were dried, filtered and concentrated in vacuo. Purification by chromatography (silica, heptane:ethyl acetate=100:0 to 2:3) afforded the title compound (481 mg, 31%) as a light yellow solid after trituration with dichloromethane. MS: m/e=339.3 [M+H]$^+$.

b) 5-(5-Methyl-3-phenyl-isoxazol-4-ylmethoxy)-pyridine-2-carboxylic acid

To a solution of 5-(5-methyl-3-phenyl-isoxazol-4-ylmethoxy)-pyridine-2-carboxylic acid ethyl ester (481 mg, 1.42 mmol) in THF (12 mL) was added a solution of lithium hydroxide monohydrate (418 mg, 9.8 mmol) in water (6 mL) and the resulting mixture stirred at room temperature overnight. The mixture was acidified with HCl (1 N, 10 mL) and evaporation afforded the title compound (335 mg, 70%) which was obtained as a light yellow solid. MS: m/e=309.0 [M−H]$^-$.

c) 5-(5-Methyl-3-phenyl-isoxazol-4-ylmethoxy)-pyridine-2-carboxylic acid N',N'-dimethyl-hydrazide To a solution of 5-(5-methyl-3-phenyl-isoxazol-4-ylmethoxy)-pyridine-2-carboxylic acid (100 mg, 0.32 mmol) in DMF (5 mL) were added 2-(1H-benzotriazole-1-yl)-1,1,3,3-tetramethyluronium tetrafluoroborate (114 mg, 0.36 mmol), N,N-diisopropyl ethyl amine (0.27 mL, 8.1 mmol) and N,N-dimethylhydrazine (21 mg, 0.35 mmol). The resulting reaction mixture was stirred overnight at room temperature. The reaction mixture was evaporated and then diluted with water and extracted with ethyl acetate. The combined organic layers were dried, filtered and concentrated in vacuo. Concentration and purification by chromatography (silica, 0 to 5% methanol

EXAMPLE 5

5-(5-Methyl-3-phenyl-isoxazol-4-ylmethoxy)-pyridine-2-carboxylic acid morpholin-4-ylamide

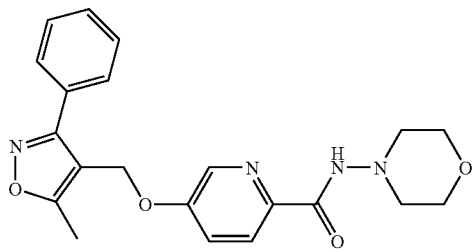 [SMILES: Cc1onc(-c2ccccc2)c1COc1ccc(C(=O)NN2CCOCC2)nc1]

As described for example 4c, 5-(5-methyl-3-phenyl-isoxazol-4-ylmethoxy)-pyridine-2-carboxylic acid (100 mg, 0.32 mmol) was converted, using N-aminomorpholine instead of N,N-dimethylhydrazine, to the title compound (62 mg, 49%) which was obtained as a light yellow oil. MS: m/e=395.3 [M+H]$^+$.

EXAMPLE 6

5-(5-Methyl-3-pyridin-2-yl-isoxazol-4-ylmethoxy)-pyridine-2-carboxylic acid (tetrahydro-pyran-4-yl)-amide

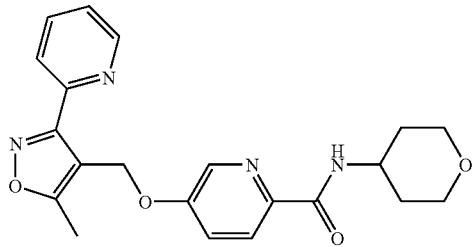 [SMILES: Cc1onc(-c2ccccn2)c1COc1ccc(C(=O)NC2CCOCC2)nc1]

a) (E)- and/or (Z)-Pyridine-2-carbaldehyde oxime

To a suspension of 2-pyridinecarboxaldehyde (53.6 g, 500 mmol) and hydroxylamine hydrochloride (38.2 g, 544 mmol) in ethanol (36 mL) and water (69 mL) was added ice (205 g). Then an aqueous solution of sodium hydroxide (32%, 115 mL, 1.24 mol) was added dropwise within a 10 min period (temperature rises from −8° C. to +7° C.) whereupon most of the solid dissolves. After 1 h stirring at room temperature the resulting mixture was then acidified with HCl (5 N). The mixture was then extracted with dichloromethane to afford the title compound (47.7 g, 78%) which was obtained as an off white solid. MS: m/e=123.3 [M+H]$^+$.

b) 5-Methyl-3-pyridin-2-yl-isoxazole-4-carboxylic acid ethyl ester

To a suspension of N-chlorosuccinimide (6.0 g, 33 mmol) in chloroform (20 mL) was added pyridine (0.26 mL, 3.3 mmol) and a solution of (E)- and/or (Z)-pyridine-2-carbaldehyde oxime (4.0 g, 33 mmol) in chloroform (103 mL) during 15 min at ambient temperature. After stirring for 30 min at this temperature a solution of ethyl (E)-3-(1-pyrrolidino)-2-butenoate (6.0 g, 33 mmol) in chloroform (4 mL) was added. The resulting suspension was warmed to 50° C. and a solution of triethylamine (12 mL, 86 mmol) in chloroform (10 mL) was added dropwise over a period of 1 h. Stirring was continued for 0.5 h at 50° C. and for 30 h at room temperature. The dark brown solution was washed with water (100 mL) and the aqueous layers were extracted with dichloromethane (50 mL) and dried over sodium sulfate and evaporated. Purification by chromatography (silica, heptane:ethyl acetate 8:2 to 1:1) afforded the title compound (4.43 g, 58%) as a yellow oil. MS: m/e=233.3 [M+H]$^+$.

c) (5-Methyl-3-pyridin-2-yl-isoxazol-4-yl)-methanol

To a solution of 5-methyl-3-pyridin-2-yl-isoxazole-4-carboxylic acid ethyl ester (4.1 g, 18 mmol) in THF (229 mL) at 0° C. was added lithium aluminium hydride (367 mg, 10 mmol). And the resulting mixture stirred for 1 h at room temperature. Water (1.9 mL) was added carefully followed by aqueous sodium hydroxide (15%, 1.9 mL) and water (0.54 mL). The resulting suspension was stirred for 15 min at ambient temperature and filtered over Hyflo®. Concentration and trituration with heptane afforded the title compound (2.88 g, 86%) as a light yellow solid. MS: m/e=191.3 [M+H]$^+$.

d) 5-(5-Methyl-3-pyridin-2-yl-isoxazol-4-ylmethoxy)-pyridine-2-carboxylic acid methyl ester To a solution of (5-methyl-3-pyridin-2-yl-isoxazol-4-yl)-methanol (100 mg, 0.53 mmol) in THF (5 mL) was added 5-hydroxy-pyridine-2-carboxylic acid methyl ester (89 mg, 0.58 mmol) and triphenylphosphine (207 mg, 0.79 mmol) at ambient temperature under an argon atmosphere. Then diethyl azodicarboxylate (362 μL, 40% solution in toluene, 0.79 mmol) was added and the reaction mixture was stirred for 3 h at room temperature. The reaction mixture was evaporated and then purified by chromatography (silica, heptane:ethyl acetate=100:0 to 2:3) to afford the title compound (78 mg, 44%) as a white solid. MS: m/e=326.1 [M+H]$^+$.

e) 5-(5-Methyl-3-pyridin-2-yl-isoxazol-4-ylmethoxy)-pyridine-2-carboxylic acid

To a solution of 5-(5-methyl-3-pyridin-2-yl-isoxazol-4-ylmethoxy)-pyridine-2-carboxylic acid methyl ester (56 mg, 0.17 mmol) in THF (0.6 mL) was added a solution of lithium hydroxide monohydrate (15 mg, 0.34 mmol) in water (0.6 mL) followed by methanol (0.2 mL) and the resulting mixture stirred at room temperature for 2 h. The mixture was then evaporated and acidified with HCl (1 N) and the mixture cooled to 0° C. for 30 min. A solid formed which was filtered off, washed with water and dried to afford the title compound (41 mg, 76%) which was obtained as a white solid. MS: m/e=310.3 [M−H]$^−$.

f) 5-(5-Methyl-3-pyridin-2-yl-isoxazol-4-ylmethoxy)-pyridine-2-carboxylic acid (tetrahydro-pyran-4-yl)-amide To a solution of 5-(5-methyl-3-pyridin-2-yl-isoxazol-4-ylmethoxy)-pyridine-2-carboxylic acid (30 mg, 0.1 mmol) in DMF (1 mL) were added 2-(1H-benzotriazole-1-yl)-1,1,3,3-tetramethyluronium tetrafluoroborate (34 mg, 0.1 mmol), N,N-diisopropyl ethyl amine (83 μL, 0.48 mmol) and 4-aminotetrahydropyran (11 mg, 0.1 mmol). The resulting reaction mixture was stirred overnight at room temperature. The reaction mixture was evaporated and purification by chromatography (silica, heptane:ethyl actate=100:0 to 2:3) afforded the title compound (29 mg, 76%) as a white solid. MS: m/e=395.2 [M+H]+.

EXAMPLE 7

5-(5-Methyl-3-pyridin-2-yl-isoxazol-4-ylmethoxy)-pyridine-2-carboxylic acid isopropyl-amide

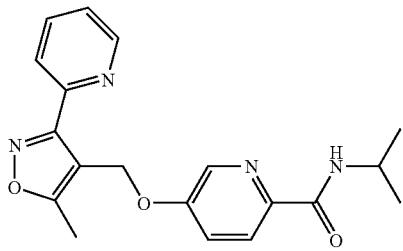 [SMILES: Cc1onc(-c2ccccn2)c1COc1ccc(C(=O)NC(C)C)nc1]

As described for example 6f, 5-(5-methyl-3-pyridin-2-yl-isoxazol-4-ylmethoxy)-pyridine-2-carboxylic acid (81.6 mg, 0.26 mmol) was converted, using isopropylamine instead of 4-aminotetrahydropyran, to the title compound (74 mg, 80%), after 1 h instead of overnight, which was obtained as a white solid after purification by chromatography (silica, heptane:ethyl acetate=4:1 to 0:1). MS: m/e=353.2 [M+H]+.

EXAMPLE 8

5-(5-Methyl-3-pyridin-2-yl-isoxazol-4-ylmethoxy)-pyridine-2-carboxylic acid (2-hydroxy-1,1-dimethyl-ethyl)-amide

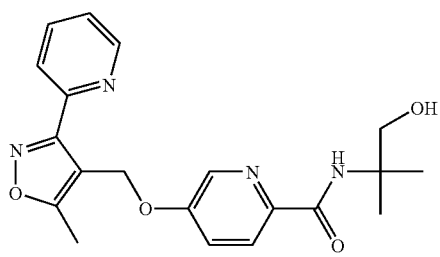 [SMILES: Cc1onc(-c2ccccn2)c1COc1ccc(C(=O)NC(C)(C)CO)nc1]

As described for example 7, 5-(5-methyl-3-pyridin-2-yl-isoxazol-4-ylmethoxy)-pyridine-2-carboxylic acid (81.6 mg, 0.26 mmol) was converted, using 2-amino-2-methyl-1-propanol instead of isopropylamine, to the title compound (84 mg, 84%), which was obtained as a white solid. MS: m/e=383.2 [M+H]+.

EXAMPLE 9

5-(5-Methyl-3-pyridin-2-yl-isoxazol-4-ylmethoxy)-pyridine-2-carboxylic acid morpholin-4-ylamide

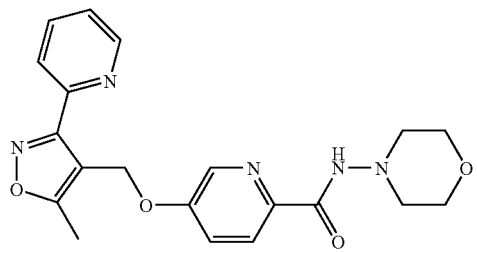 [SMILES: Cc1onc(-c2ccccn2)c1COc1ccc(C(=O)NN2CCOCC2)nc1]

As described for example 7, 5-(5-methyl-3-pyridin-2-yl-isoxazol-4-ylmethoxy)-pyridine-2-carboxylic acid (81.6 mg, 0.26 mmol) was converted, using N-aminomorpholine instead of isopropylamine, to the title compound (85 mg, 82%), which was obtained as a white solid. MS: m/e=396.2 [M+H]+.

EXAMPLE 10

(1,1-Dioxo-1,6-thiomorpholin-4-yl)-[5-(5-methyl-3-pyridin-2-yl-isoxazol-4-ylmethoxy)-pyridin-2-yl]-methanone

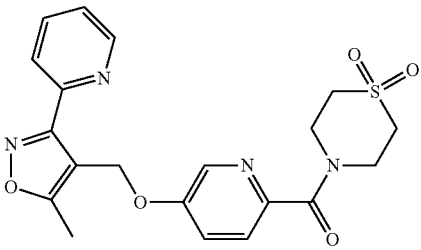 [SMILES: Cc1onc(-c2ccccn2)c1COc1ccc(C(=O)N2CCS(=O)(=O)CC2)nc1]

As described for example 7, 5-(5-methyl-3-pyridin-2-yl-isoxazol-4-ylmethoxy)-pyridine-2-carboxylic acid (81.6 mg, 0.26 mmol) was converted, using thiomorpholine 1,1-dioxide instead of isopropylamine, to the title compound (60 mg, 53%), which was obtained as a white solid after recrystallization from ethyl acetate. MS: m/e=429.2 [M+H]+.

EXAMPLE 11

5-(5-Methyl-3-pyridin-2-yl-isoxazol-4-ylmethoxy)-pyridine-2-carboxylic acid cyclopropyl amide

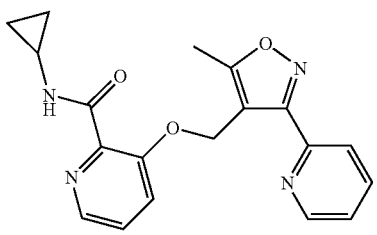 [SMILES: Cc1onc(-c2ccccn2)c1COc1cccnc1C(=O)NC1CC1]

As described for example 7, 5-(5-methyl-3-pyridin-2-yl-isoxazol-4-ylmethoxy)-pyridine-2-carboxylic acid (81.6 mg, 0.26 mmol) was converted, using cyclopropylamine instead of isopropylamine, to the title compound (81 mg, 88%), which was obtained as a white solid. MS: m/e=351.3 [M+H]$^+$.

EXAMPLE 12

5-(5-Methyl-3-pyridin-2-yl-isoxazol-4-ylmethoxy)-pyridine-2-carboxylic acid cyclopropyl-methyl-amide

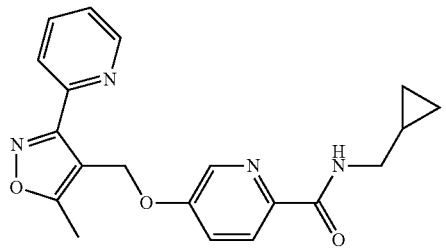 [SMILES: Cc1onc(-c2ccccn2)c1COc1ccc(C(=O)NCC2CC2)nc1]

As described for example 7, 5-(5-methyl-3-pyridin-2-yl-isoxazol-4-ylmethoxy)-pyridine-2-carboxylic acid (100 mg, 0.32 mmol) was converted, using aminomethylcyclopropane instead of isopropylamine, to the title compound (105 mg, 89%), which was obtained as a white solid. MS: m/e=365.1 [M+H]$^+$.

EXAMPLE 13

5-(5-Methyl-3-pyridin-2-yl-isoxazol-4-ylmethoxy)-pyridine-2-carboxylic acid (2,2,2-trifluoro-ethyl)-amide

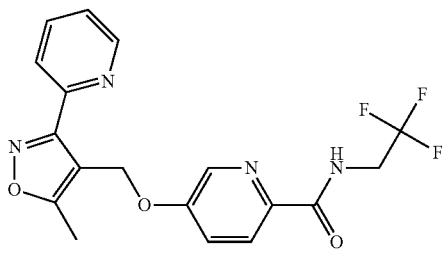 [SMILES: Cc1onc(-c2ccccn2)c1COc1ccc(C(=O)NCC(F)(F)F)nc1]

As described for example 7, 5-(5-methyl-3-pyridin-2-yl-isoxazol-4-ylmethoxy)-pyridine-2-carboxylic acid (100 mg, 0.32 mmol) was converted, using 2,2,2-trifluoroethylamine instead of isopropylamine, to the title compound (111 mg, 88%), which was obtained as a white solid. MS: m/e=393.2 [M+H]$^+$.

EXAMPLE 14

5-(5-Methyl-3-pyridin-2-yl-isoxazol-4-ylmethoxy)-pyridine-2-carboxylic acid (2-hydroxy-ethyl)-amide

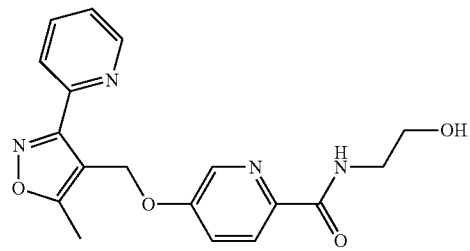 [SMILES: Cc1onc(-c2ccccn2)c1COc1ccc(C(=O)NCCO)nc1]

As described for example 7, 5-(5-methyl-3-pyridin-2-yl-isoxazol-4-ylmethoxy)-pyridine-2-carboxylic acid (100 mg, 0.32 mmol) was converted, using ethanolamine instead of isopropylamine, to the title compound (110 mg, 96%), which was obtained as a white solid. MS: m/e=355.2 [M+H]$^+$.

EXAMPLE 15

5-(5-Methyl-3-pyridin-2-yl-isoxazol-4-ylmethoxy)-pyridine-2-carboxylic acid ethylamide

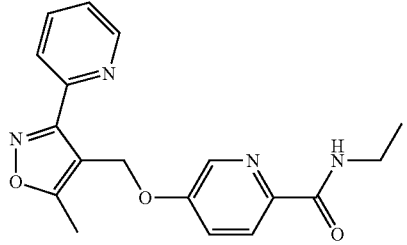

As described for example 7, 5-(5-methyl-3-pyridin-2-yl-isoxazol-4-ylmethoxy)-pyridine-2-carboxylic acid (100 mg, 0.32 mmol) was converted, using ethylamine (2 M solution in THF) instead of isopropylamine, to the title compound (93 mg, 85%), which was obtained as a white solid. MS: m/e=339.1 [M+H]$^+$.

EXAMPLE 16

5-(5-Methyl-3-pyridin-2-yl-isoxazol-4-ylmethoxy)-pyridine-2-carboxylic acid methylamide

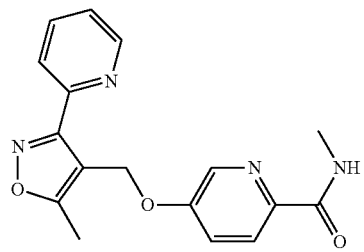 [SMILES: CNC(=O)c1ccc(OCc2c(-c3ccccn3)noc2C)cn1]

As described for example 7, 5-(5-methyl-3-pyridin-2-yl-isoxazol-4-ylmethoxy)-pyridine-2-carboxylic acid (100 mg, 0.32 mmol) was converted, using methylamine (2 M solution in THF) instead of isopropylamine, to the title compound (81 mg, 78%), which was obtained as a white solid. MS: m/e=325.2 [M+H]⁺.

EXAMPLE 17

[5-(5-Methyl-3-pyridin-2-yl-isoxazol-4-ylmethoxy)-pyridin-2-yl]-thiomorpholin-4-yl-methanone

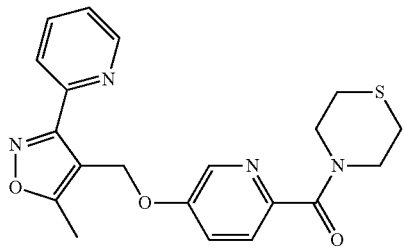 [SMILES: Cc1onc(-c2ccccn2)c1COc1ccc(C(=O)N2CCSCC2)nc1]

As described for example 7, 5-(5-methyl-3-pyridin-2-yl-isoxazol-4-ylmethoxy)-pyridine-2-carboxylic acid (100 mg, 0.32 mmol) was converted, using thiomorpholine instead of isopropylamine, to the title compound (125 mg, 98%), which was obtained as a white solid. MS: m/e=397.2 [M+H]⁺.

EXAMPLE 18

5-(5-Methyl-3-pyridin-2-yl-isoxazol-4-ylmethoxy)-pyridine-2-carboxylic acid ((1S,2S)-2-hydroxy-cyclopentyl)-amide

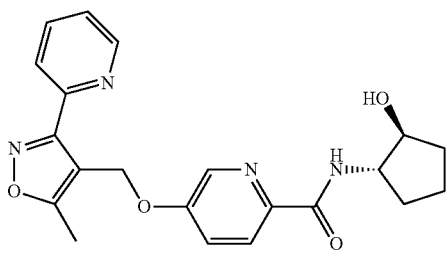 [SMILES: Cc1onc(-c2ccccn2)c1COc1ccc(C(=O)N[C@H]2CCC[C@@H]2O)nc1]

As described for example 7, 5-(5-methyl-3-pyridin-2-yl-isoxazol-4-ylmethoxy)-pyridine-2-carboxylic acid (100 mg, 0.32 mmol) was converted, using trans-2-aminocyclopentanol hydrochloride instead of isopropylamine, to the title compound (100 mg, 78%), which was obtained as a white solid. MS: m/e=395.1 [M+H]⁺.

EXAMPLE 19

5-(5-Methyl-3-pyridin-2-yl-isoxazol-4-ylmethoxy)-pyridine-2-carboxylic acid (1-methyl-1H-pyrazol-4-yl)-amide

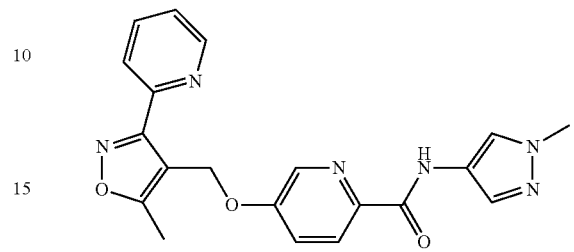

As described for example 7, 5-(5-methyl-3-pyridin-2-yl-isoxazol-4-ylmethoxy)-pyridine-2-carboxylic acid (100 mg, 0.32 mmol) was converted, using 1-methyl-1H-pyrazol-4-ylamine dihydrochloride instead of isopropylamine, to the title compound (113 mg, 90%), which was obtained as a white solid. MS: m/e=391.1 [M+H]⁺.

EXAMPLE 20

Rac-5-(5-Methyl-3-pyridin-2-yl-isoxazol-4-ylmethoxy)-pyridine-2-carboxylic acid (1-hydroxymethyl-propyl)-amide

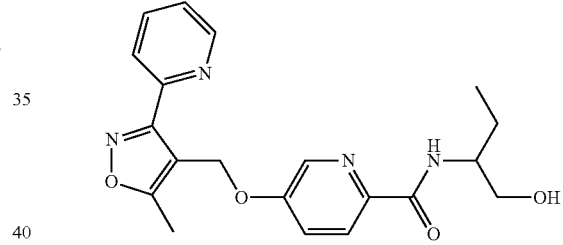

As described for example 7, 5-(5-methyl-3-pyridin-2-yl-isoxazol-4-ylmethoxy)-pyridine-2-carboxylic acid (100 mg, 0.32 mmol) was converted, using rac-2-amino-1-butanol instead of isopropylamine, to the title compound (87 mg, 70%), which was obtained as a white solid. MS: m/e=383.2 [M+H]⁺.

EXAMPLE 21

5-(5-Methyl-3-pyridin-2-yl-isoxazol-4-ylmethoxy)-pyridine-2-carboxylic acid ((S)-1-hydroxymethyl-propyl)-amide

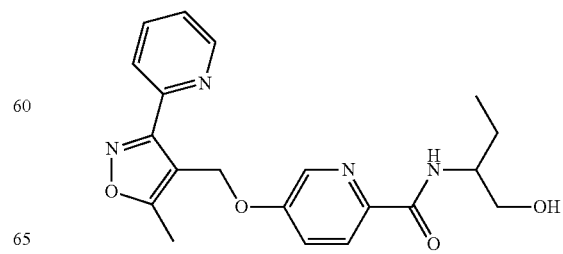

As described for example 7, 5-(5-methyl-3-pyridin-2-yl-isoxazol-4-ylmethoxy)-pyridine-2-carboxylic acid (100 mg, 0.32 mmol) was converted, using S-(+)-2-amino-1-butanol instead of isopropylamine, to the title compound (89 mg, 72%), which was obtained as a white solid. MS: m/e=383.2 [M+H]$^+$.

EXAMPLE 22

5-(5-Methyl-3-pyridin-2-yl-isoxazol-4-ylmethoxy)-pyridine-2-carboxylic acid ((S)-2,2,2-trifluoro-1-methyl-ethyl)-amide

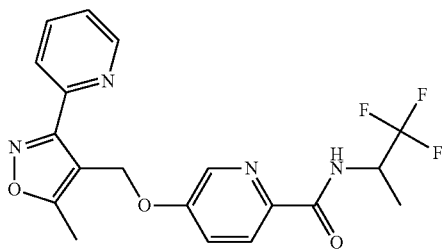 [SMILES: Cc1onc(-c2ccccn2)c1COc1ccc(C(=O)NC(C)C(F)(F)F)nc1]

As described for example 7, 5-(5-methyl-3-pyridin-2-yl-isoxazol-4-ylmethoxy)-pyridine-2-carboxylic acid (100 mg, 0.32 mmol) was converted, using L-2,2,2-trifluoro-1-(methyl)ethylamine instead of isopropylamine, to the title compound (92 mg, 70%), which was obtained as a white solid. MS: m/e=407.2 [M+H]$^+$.

EXAMPLE 23

5-[3-(5-Fluoro-pyridin-2-yl)-5-methyl-isoxazol-4-ylmethoxy]-pyridine-2-carboxylic acid isopropylamide

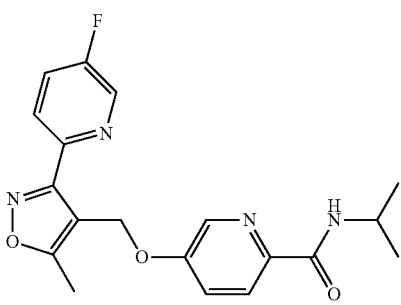 [SMILES: Cc1onc(-c2ccc(F)cn2)c1COc1ccc(C(=O)NC(C)C)nc1]

a) 5-Fluoro-pyridine-2-carbaldehyde oxime

To a solution of 5-fluoro-2-formylpyridine (5.0 g, 41 mmol) and hydroxylamine hydrochloride (3.06 g, 44 mmol) in ethanol (3.2 mL) and water (9.6 mL) was added ice (18.6 g). Then a solution of NaOH (4.0 g, 100 mmol) in water (4.6 mL) was added dropwise over 10 min keeping the temperature between −5° C. and +5° C. The reaction mixture was then stirred at room temperature for 30 min. Then HCl (4N) was added to acidify the mixture and the resulting precipitate was filtered off and washed with water to afford the title compound (4.41 g, 79%) as a light brown solid. MS: m/e=141.0 [M+H]$^+$.

b) 3-(5-Fluoro-pyridin-2-yl)-5-methyl-isoxazole-4-carboxylic acid ethyl ester

To a suspension of N-chlorosuccinimide (4.63 g, 35 mmol) in chloroform (21 mL) was added pyridine (0.28 mL, 3.5 mmol) and a solution of 5-fluoro-pyridine-2-carbaldehyde oxime (4.86 g, 35 mmol) in chloroform (110 mL) during 15 min at room temperature. After stirring for 30 min at this temperature a solution of ethyl (E)-3-(1-pyrrolidino)-2-butenoate (6.36 g, 35 mmol) in chloroform (4.4 mL) was added. The resulting suspension was warmed to 50° C. and a solution of triethylamine (4.83 mL, 35 mmol) in chloroform (4.4 mL) was added dropwise over a period of 30 min. Stirring was continued for 1.5 h at 50° C. and then cooled to ambient temperature. The solution was then diluted with ice-water (200 mL) and the aqueous layers were extracted with dichloromethane (50 mL) and dried over sodium sulfate and evaporation to give a dark brown oil. Purification by chromatography (silica, heptane:ethyl acetate=100:0 to 20:80) afforded the title compound (5.83 g, 67%) as yellow oil. MS: m/e=251.1 [M+H]$^+$.

c) [3-(5-Fluoro-pyridin-2-yl)-5-methyl-isoxazol-4-yl]-methanol

To a solution of 3-(5-fluoro-pyridin-2-yl)-5-methyl-isoxazole-4-carboxylic acid ethyl ester (2.5 g, 10 mmol) in dry THF (34 mL), cooled to 0° C., was added lithiumaluminumhydride (209 mg, 2.3 mmol) portionwise. After allowing to warm up to room temperature over 1 h, the mixture was cooled to 0° C. and water (0.2 mL) was added carefully followed by aqueous sodium hydroxide (15%, 0.2 mL) and water (0.6 mL). The resulting suspension was stirred for 4 h at ambient temperature and filtered over Hyflo®. The filtrate was then concentrated and purification by chromatography (silica, heptane:ethyl acetate=50:50 to 0:100) afforded the title compound (1.47 g, 71%) as a light yellow solid. MS: m/e=209.1 [M+H]$^+$.

d) 5-[3-(5-Fluoro-pyridin-2-yl)-5-methyl-isoxazol-4-ylmethoxy]-pyridine-2-carboxylic acid methyl ester To a solution of [3-(5-fluoro-pyridin-2-yl)-5-methyl-isoxazol-4-yl]-methanol (854 mg, 4.1 mmol) in THF (40 mL) was added 5-hydroxy-pyridine-2-carboxylic acid methyl ester (691 mg, 4.5 mmol) and triphenylphosphine (1.61 g, 6.1 mmol) at ambient temperature under an argon atmosphere. Then diethyl azodicarboxylate (2.82 mL, 40% solution in toluene, 6.0 mmol) was added and the reaction mixture was stirred for 2 h at room temperature. The reaction mixture was evaporated and then purified by chromatography (silica, heptane:ethyl acetate=100:0 to 2:3) to afford the title compound (1.53 g, 76%) as an off white solid. MS: m/e=344.0 [M+H]$^+$.

e) 5-[3-(5-Fluoro-pyridin-2-yl)-5-methyl-isoxazol-4-ylmethoxy]-pyridine-2-carboxylic acid To a solution of 5-[3-(5-fluoro-pyridin-2-yl)-5-methyl-isoxazol-4-ylmethoxy]-pyridine-2-carboxylic acid methyl ester (540 mg, 1.42 mmol) in THF (5.4 mL) was added a solution of lithium hydroxide monohydrate (118 mg, 2.83 mmol) in water (5.4 mL) followed by methanol (2 mL) and the resulting mixture stirred at room temperature overnight. The mixture was then evaporated and acidified with HCl (1 N) and the mixture cooled to 0° C. for 30 min. A solid formed which was filtered off, washed with water and dried to afford f) 5-[3-(5-Fluoro-pyridin-2-yl)-5-methyl-isoxazol-4-ylmethoxy]-pyridine-2-carboxylic acid isopropylamide To a solution of 5-[3-(5-fluoro-pyridin-2-yl)-5-methyl-isoxazol-4-ylmethoxy]-pyridine-2-carboxylic acid (75 mg, 0.23 mmol) in DMF (2 mL) were added 2-(1H-benzotriazole-1-yl)-1,1,3,3-tetramethyluronium tetrafluoroborate (81 mg, 0.25 mmol), N,N-diisopropyl ethyl amine (195 μL, 1.14 mmol) and isopropylamine (22 μL, 0.25 mmol). The resulting reaction mixture was stirred at room temperature for 1 h. The reaction mixture was evaporated and purification by chromatography (silica, heptane:ethyl acetate=100:0 to 2:3) afforded the title compound (60 mg, 71%) as a white solid. MS: m/e=371.1 [M+H]⁺.

EXAMPLE 24

5-[3-(5-Fluoro-pyridin-2-yl)-5-methyl-isoxazol-4-ylmethoxy]-pyridine-2-carboxylic acid (2-hydroxy-1,1-dimethyl-ethyl)-amide

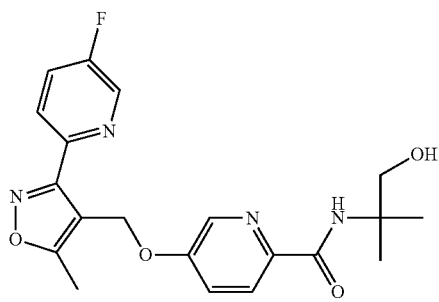 [SMILES: Cc1onc(-c2ccc(F)cn2)c1COc1ccc(C(=O)NC(C)(C)CO)nc1]

As described for example 23f, 5-[3-(5-fluoro-pyridin-2-yl)-5-methyl-isoxazol-4-ylmethoxy]-pyridine-2-carboxylic acid (75 mg, 0.23 mmol) was converted, using 2-amino-2-methyl-1-propanol instead of isopropylamine, to the title compound (60 mg, 66%), which was obtained as a light-bluish solid. MS: m/e=401.4 [M+H]⁺.

EXAMPLE 25

5-[3-(5-Fluoro-pyridin-2-yl)-5-methyl-isoxazol-4-ylmethoxy]-pyridine-2-carboxylic acid morpholin-4-ylamide

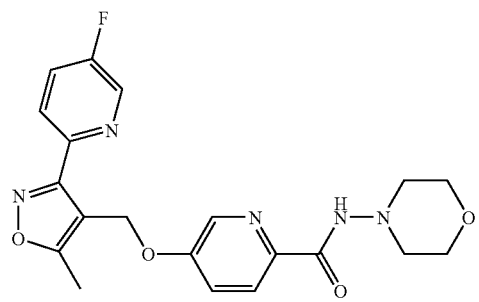 [SMILES: Cc1onc(-c2ccc(F)cn2)c1COc1ccc(C(=O)NN2CCOCC2)nc1]

As described for example 23f, 5-[3-(5-fluoro-pyridin-2-yl)-5-methyl-isoxazol-4-ylmethoxy]-pyridine-2-carboxylic acid (75 mg, 0.23 mmol) was converted, using 4-aminomorpholine instead of isopropylamine, to the title compound (57 mg, 60%), which was obtained as a white solid after recrystallization from ethyl acetate/hexane. MS: m/e=414.3 [M+H]⁺.

EXAMPLE 26

(1,1-Dioxo-1,6-thiomorpholin-4-yl)-{5-[3-(5-fluoro-pyridin-2-yl)-5-methyl-isoxazol-4-ylmethoxy]-pyridin-2-yl}-methanone

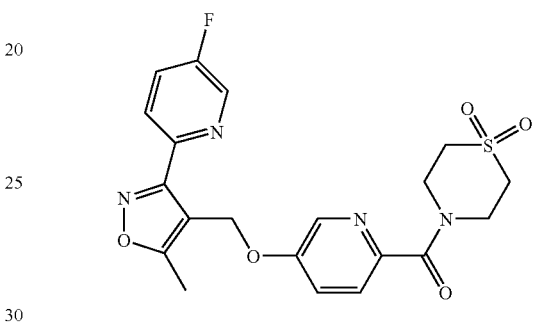

As described for example 23f, 5-[3-(5-fluoro-pyridin-2-yl)-5-methyl-isoxazol-4-ylmethoxy]-pyridine-2-carboxylic acid (75 mg, 0.23 mmol) was converted, using thiomorpholine 1,1-dioxide instead of isopropylamine, to the title compound (87 mg, 86%), which was obtained as a white solid. MS: m/e=447.1 [M+H]⁺.

EXAMPLE 27

5-[3-(5-Fluoro-pyridin-2-yl)-5-methyl-isoxazol-4-ylmethoxy]-pyridine-2-carboxylic acid cyclopropylamide

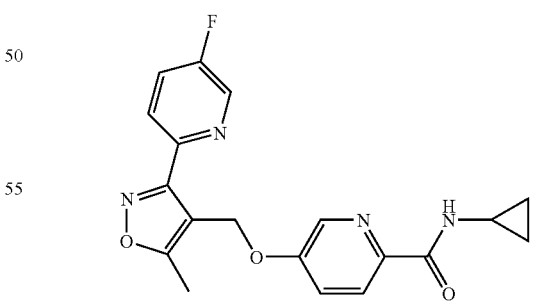

As described for example 23f, 5-[3-(5-fluoro-pyridin-2-yl)-5-methyl-isoxazol-4-ylmethoxy]-pyridine-2-carboxylic acid (75 mg, 0.23 mmol) was converted, using cyclopropylamine instead of isopropylamine, to the title compound (63 mg, 75%), which was obtained as a white solid. MS: m/e=369.2 [M+H]⁺.

EXAMPLE 28

5-[3-(5-Fluoro-pyridin-2-yl)-5-methyl-isoxazol-4-ylmethoxy]-pyridine-2-carboxylic acid (2,2,2-trifluoro-ethyl)-amide

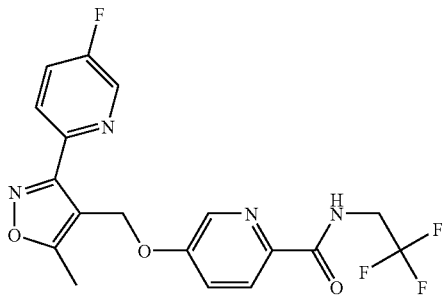 [SMILES: Cc1onc(-c2ccc(F)cn2)c1COc1ccc(C(=O)NCC(F)(F)F)nc1]

As described for example 23f, 5-[3-(5-fluoro-pyridin-2-yl)-5-methyl-isoxazol-4-ylmethoxy]-pyridine-2-carboxylic acid (75 mg, 0.23 mmol) was converted, using 2,2,2-trifluorethylamine instead of isopropylamine, to the title compound (68 mg, 73%), which was obtained as a white solid. MS: m/e=411.2 [M+H]$^+$.

EXAMPLE 29

5-[3-(4-Fluoro-phenyl)-5-hydroxymethyl-isoxazol-4-ylmethoxy]-pyridine-2-carboxylic acid isopropylamide

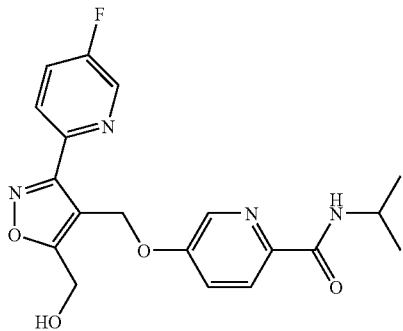 [SMILES: CC(C)NC(=O)c1ccc(OCc2c(-c3ccc(F)cn3)noc2CO)cn1]

a) 3-(4-Fluoro-phenyl)-5-((E)-styryl)-isoxazole-4-carboxylic acid

To a solution of 3-(4-fluoro-phenyl)-5-methyl-isoxazole-4-carboxylic acid ethyl ester (20.0 g, 80.2 mmol) and benzaldehyde (8.19 mL, 80.2 mmol) in ethanol (113 mL) was added sodium ethoxide (2.71M, 32.5 mL, 88.3 mmol) and the reaction mixture was heated under reflux for 1 h. Hydrochloric acid (1 N, 96.3 mL) was added and the resulting mixture was extracted with toluene. The solvent was then distilled off to afford the title compound (19.1 g, 77%) as a light yellow solid. MS: m/e=308.0 [M−H]$^−$.

b) [3-(4-Fluoro-phenyl)-5-((E)-styryl)-isoxazole-4-yl]-methanol

To a solution of 3-(4-fluoro-phenyl)-5-((E)-styryl)-isoxazole-4-carboxylic acid (19.0 g, 61.4 mmol) and triethylamine (8.6 mL, 61.4 mmol) in THF (475 mL) was added at room temperature a solution of ethyl chloroformate (5.97 mL, 61.4 mmol) in THF (55 mL). After 1 h the triethylamine hydrochloride salt was filtered off and washed with a small amount of THF. The mixture was added to a solution of sodium borohydride (6.05 g, 154 mmol) and water (55 mL). After stirring overnight at room temperature aqueous sodium hydroxide solution (1 N, 180 mL) was added. Extraction with tert-butylmethylether, removal of the solvent by distillation and chromatography (silica, dichloromethane:methanol=1:0 to 95:5) afforded the title compound (11.4 g, 63%) as light yellow solid. MS: m/e=296.2 [M+H]$^+$.

c) 5-[3-(4-Fluoro-phenyl)-5-((E)-styryl)-isoxazol-4-ylmethoxy]-pyridine-2-carboxylic acid ethyl ester To a stirred solution of [3-(4-fluoro-phenyl)-5-((E)-styryl)-isoxazol-4-yl]-methanol (4.0 g, 13.5 mmol) and 5-hydroxy-pyridine-2-carboxylic acid ethyl ester (2.49 g, 14.9 mmol) in THF (130 mL) under argon was added triphenylphosphine (5.49 g, 20.31 mmol). Diethyl azodicarboxylate (9.3 mL, 20.31 mmol) was then added dropwise. After 3 h the reaction mixture was concentrated then purified by chromatography (silica, 10 to 40% ethyl actetate in heptane) afforded the title compound (2.85 g, 47%) as a white solid. MS: m/e=445.4 [M+H]$^+$.

d) 5-[3-(4-Fluoro-phenyl)-5-formyl-isoxazol-4-ylmethoxy]-pyridine-2-carboxylic acid ethyl ester A mixture of 5-[3-(4-fluoro-phenyl)-5-((E)-styryl)-isoxazol-4-ylmethoxy]-pyridine-2-carboxylic acid ethyl ester (2.0 g, 4.5 mmol), osmium(VIII) oxide (28.6 mg, 0.11 mmol), sodium metaperiodate (3.85 g, 18 mmol), benzyltriethylammonium chloride (418 mg, 1.8 mmol) in dioxane (30 mL) and water (10 mL) was irradiated in the microwave for 15 min at 120° C. Extractive workup (ethyl acetate/water) was followed by drying of the organic phase over sodium sulfate, filtered and concentrated. Purification by chromatography (silica, heptane:ethyl acetate=4:1 to 1:1) afforded the title compound (1.2 g, 72%) as a colourless gum. MS: m/e=371.1 [M+H]$^+$.

e) 5-[3-(4-Fluoro-phenyl)-5-hydroxymethyl-isoxazol-4-ylmethoxy]-pyridine-2-carboxylic acid ethyl ester A solution of 5-[3-(4-fluoro-phenyl)-5-((E)-styryl)-isoxazol-4-ylmethoxy]-pyridine-2-carboxylic acid ethyl ester (1.2 g, 3.24 mmol) in methanol (60 mL) was treated at room temperature with sodium borohydride (255.4 mg, 6.48 mmol) and stirred for 1 h. After quenching with aqueous citric acid (100 mL of a 10% solution) and extraction with ethyl acetate the organic phase was dried over sodium sulfate, filtered and concentrated. Purification by chromatography (silica, heptane:ethyl acetete=1:1 to 0:1) afforded the title compound as a white solid (710 mg, 59%). MS: m/e=373.2 [M+H]$^+$.

f) 5-[3-(4-Fluoro-phenyl)-5-hydroxymethyl-isoxazol-4-ylmethoxy]-pyridine-2-carboxylic acid isopropylamide To a stirred solution of isopropylamine (47.8 mg, 0.8 mmol) in dioxane (3.75 mL) was added dropwise a trimethylaluminium (603 μL, 2 M solution in toluene, 1.21 mmol) and the resulting solution stirred under argon for 30 min. A solution of 5-[3-(4-fluoro-phenyl)-5-hydroxymethyl-isoxazol-4-ylmethoxy]-pyridine-2-carboxylic acid ethyl ester (75 mg, 0.2 mmol) in dioxane (3.75 mL) was then added and the resulting solution stirred under argon for a further 1 h at 50° C. The reaction mixture was cooled and concentrated in vacuo. Purification by chromatography (silica, 0 to 10% methanol in dichloromethane) gave the title compound (17 mg, 21%) as a colourless gum. MS: m/e=386.2 [M+H]⁺.

EXAMPLE 30

5-[3-(4-Fluoro-phenyl)-5-hydroxymethyl-isoxazol-4-ylmethoxy]-pyridine-2-carboxylic acid (tetrahydro-pyran-4-yl)-amide

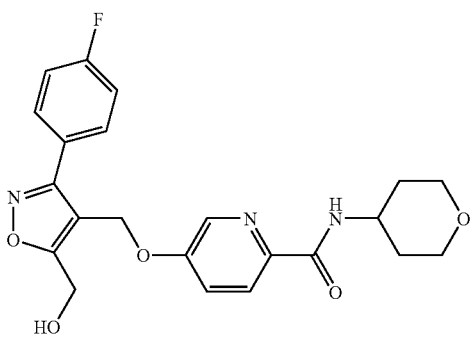 [SMILES: O=C(NC1CCOCC1)c1ccc(OCc2c(-c3ccc(F)cc3)noc2CO)cn1]

As described for example 29e, 5-[3-(4-fluoro-phenyl)-5-hydroxymethyl-isoxazol-4-ylmethoxy]-pyridine-2-carboxylic acid ethyl ester (75 mg, 0.2 mmol) was converted, using 4-aminotetrahydropyran instead of isopropylamine, to the title compound (9 mg, 10%), which was obtained as a colourless gum. MS: m/e=428.3 [M+H]⁺.

EXAMPLE 31

5-[3-(4-Fluoro-phenyl)-5-hydroxymethyl-isoxazol-4-ylmethoxy]-pyridine-2-carboxylic acid cyclopropylamide

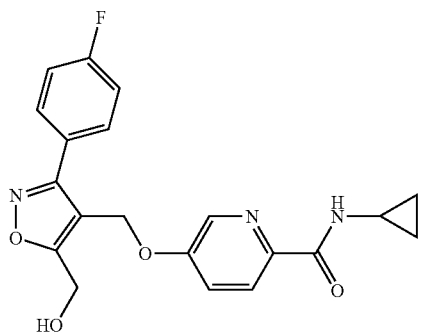 [SMILES: O=C(NC1CC1)c1ccc(OCc2c(-c3ccc(F)cc3)noc2CO)cn1]

As described for example 29e, 5-[3-(4-fluoro-phenyl)-5-hydroxymethyl-isoxazol-4-ylmethoxy]-pyridine-2-carboxylic acid ethyl ester (75 mg, 0.2 mmol) was converted, at 85° C. overnight, using cyclopropylamine instead of isopropylamine, to the title compound (20 mg, 26%), which was obtained as a colourless gum. MS: m/e=384.2 [M+H]⁺.

EXAMPLE 32

5-[3-(4-Fluoro-phenyl)-5-hydroxymethyl-isoxazol-4-ylmethoxy]-pyridine-2-carboxylic acid (2,2,2-trifluoro-1-methyl-ethyl)-amide

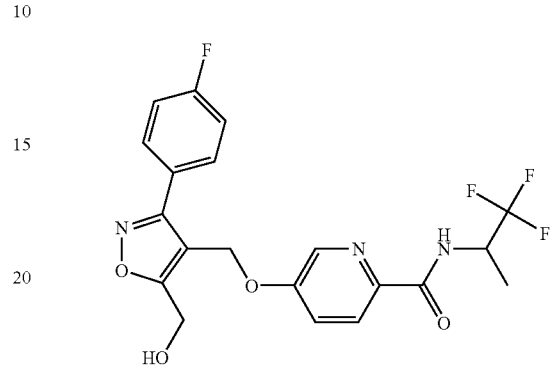

As described for example 31, 5-[3-(4-fluoro-phenyl)-5-hydroxymethyl-isoxazol-4-ylmethoxy]-pyridine-2-carboxylic acid ethyl ester (75 mg, 0.2 mmol) was converted, using 1,1,1-trifluoro-isopropylamine instead of isopropylamine, to the title compound (7 mg, 8%), which was obtained as a colourless gum. MS: m/e=440.3 [M+H]⁺.

EXAMPLE 33

5-[3-(4-Fluoro-phenyl)-5-hydroxymethyl-isoxazol-4-ylmethoxy]-pyridine-2-carboxylic acid (2,2,2-trifluoro-ethyl)-amide

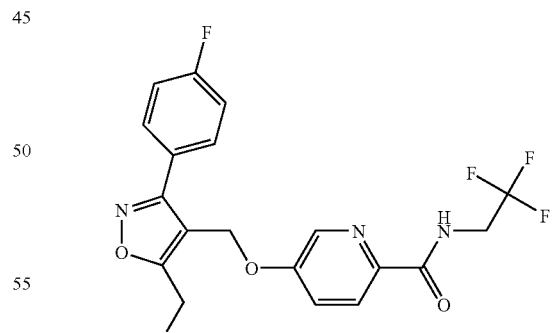

As described for example 31, 5-[3-(4-fluoro-phenyl)-5-hydroxymethyl-isoxazol-4-ylmethoxy]-pyridine-2-carboxylic acid ethyl ester (75 mg, 0.2 mmol) was converted, using 2,2,2-trifluoroethylamine instead of 1,1,1-trifluoro-isopropylamine, to the title compound (70 mg, 81%), which was obtained as a colourless gum. MS: m/e=426.2 [M+H]⁺.

EXAMPLE 34

5-[3-(4-Fluoro-phenyl)-5-hydroxymethyl-isoxazol-4-ylmethoxy]-pyridine-2-carboxylic acid ((S)-1-hydroxymethyl-propyl)-amide

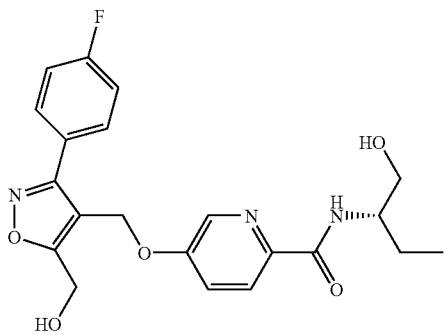 [SMILES: CC[C@@H](CO)NC(=O)c1ccc(OCc2c(-c3ccc(F)cc3)noc2CO)cn1]

a) 5-[3-(4-Fluoro-phenyl)-5-hydroxymethyl-isoxazol-4-ylmethoxy]-pyridine-2-carboxylic acid To a solution of 5-[3-(4-fluoro-phenyl)-5-hydroxymethyl-isoxazol-4-ylmethoxy]-pyridine-2-carboxylic acid ethyl ester (5.8 g, 15.6 mmol) in THF (39 mL) was added a solution of lithium hydroxide monohydrate (762 mg, 31.2 mmol) in water (36 mL) and MeOH (10 mL) and the resulting mixture stirred at room temperature for 2 h. The mixture was acidified with HCl (1 N, 30 mL) and extracted with ethyl acetate. The organic phase was dried over sodium sulfate, filtered and concentrated to afford the title compound (660 mg, 12%) which was obtained as a white solid. MS: m/e=343.0 [M−H]$^-$.

b) 5-[3-(4-Fluoro-phenyl)-5-hydroxymethyl-isoxazol-4-ylmethoxy]-pyridine-2-carboxylic acid ((S)-1-hydroxymethyl-propyl)-amide To a solution of 5-[3-(4-fluoro-phenyl)-5-hydroxymethyl-isoxazol-4-ylmethoxy]-pyridine-2-carboxylic acid (75 mg, 0.22 mmol) in THF (2 mL) was added 1-hydroxy-benzotriazole hydrate (34.1 mg, 0.22 mmol), N-ethyldiisopropylamine (95.2 µL, 0.55 mmol), N-(3-dimethylaminopropyl)-N'-ethylcarbodiimide hydrochloride (42.6 mg, 0.22 mmol) and S-(+)-1-amino-2-propanol (16.7 mg, 0.22 mmol). The reaction mixture was stirred overnight at room temperature. Evaporation of the mixture followed by chromatography (silica, dichloro-methane:methanol=1:0 to 9:1) afforded the title compound (50 mg, 55%) as a colourless gum. MS: m/e=416.2 [M+H]$^+$.

EXAMPLE 35

5-[3-(4-Fluoro-phenyl)-5-hydroxymethyl-isoxazol-4-ylmethoxy]-pyridine-2-carboxylic acid (1-methyl-1H-pyrazol-4-yl)-amide

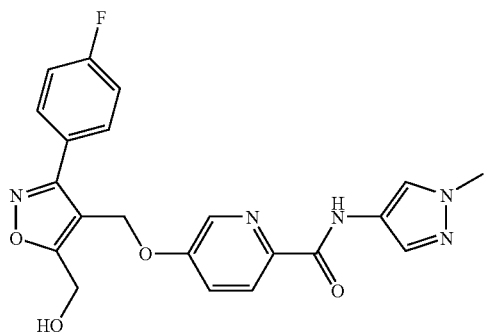 [SMILES: Cn1cc(NC(=O)c2ccc(OCc3c(-c4ccc(F)cc4)noc3CO)cn2)cn1]

As described for example 34b, 5-[3-(4-fluoro-phenyl)-5-hydroxymethyl-isoxazol-4-ylmethoxy]-pyridine-2-carboxylic acid (75 mg, 0.22 mmol) was converted, using 1-methyl-1H-pyrazol-4-ylamine instead of S-(+)-1-amino-2-propanol, to the title compound (50 mg, 54%), which was obtained as a colourless gum. MS: m/e=424.2 [M+H]$^+$.

EXAMPLE 36

5-[3-(4-Fluoro-phenyl)-5-hydroxymethyl-isoxazol-4-ylmethoxy]-pyridine-2-carboxylic acid tert-butylamide

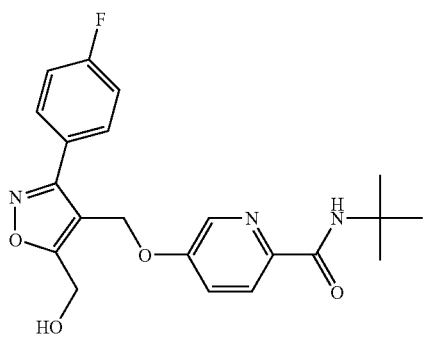 [SMILES: CC(C)(C)NC(=O)c1ccc(OCc2c(-c3ccc(F)cc3)noc2CO)cn1]

As described for example 34b, 5-[3-(4-fluoro-phenyl)-5-hydroxymethyl-isoxazol-4-ylmethoxy]-pyridine-2-carboxylic acid (75 mg, 0.22 mmol) was converted, using tert-butylamine instead of S-(+)-1-amino-2-propanol, to the title compound (45 mg, 51%), which was obtained as a colourless gum. MS: m/e=400.2 [M+H]$^+$.

EXAMPLE 37

(4,4-Difluoro-piperidin-1-yl)-{5-[3-(4-fluoro-phenyl)-5-hydroxymethyl-isoxazol-4-ylmethoxy]-pyridin-2-yl}-methanone

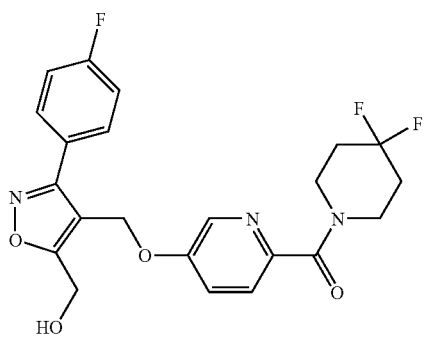 [SMILES: O=C(c1ccc(OCc2c(-c3ccc(F)cc3)noc2CO)cn1)N1CCC(F)(F)CC1]

As described for example 34b, 5-[3-(4-fluoro-phenyl)-5-hydroxymethyl-isoxazol-4-ylmethoxy]-pyridine-2-carboxylic acid (75 mg, 0.22 mmol) was converted, using 4,4-difluoropiperidine hydrochloride instead of S-(+)-1-amino-2-propanol, to the title compound (45 mg, 31%), which was obtained as a colourless gum. MS: m/e=448.2 [M+H]$^+$.

49

EXAMPLE 38

5-[3-(4-Fluoro-phenyl)-5-hydroxymethyl-isoxazol-4-ylmethoxy]-pyridine-2-carboxylic acid pyrrolidin-1-ylamide

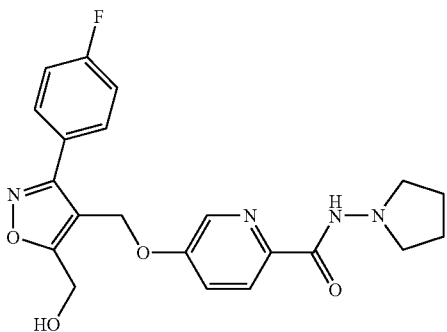 [SMILES: O=C(NN1CCCC1)c1ccc(OCc2c(-c3ccc(F)cc3)noc2CO)cn1]

As described for example 34b, 5-[3-(4-fluoro-phenyl)-5-hydroxymethyl-isoxazol-4-ylmethoxy]-pyridine-2-carboxylic acid (100 mg, 0.29 mmol) was converted, using 1-aminopyrrolidine hydrochloride instead of S-(+)-1-amino-2-propanol, to the title compound (31 mg, 23%), which was obtained as a white solid. MS: m/e=413.2 [M+H]$^+$.

EXAMPLE 39

5-[3-(4-Fluoro-phenyl)-5-hydroxymethyl-isoxazol-4-ylmethoxy]-pyridine-2-carboxylic acid morpholin-4-ylamide

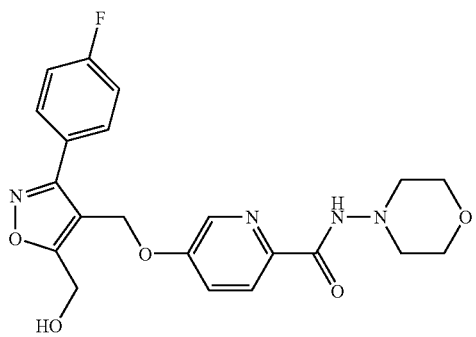 [SMILES: O=C(NN1CCOCC1)c1ccc(OCc2c(-c3ccc(F)cc3)noc2CO)cn1]

As described for example 34b, 5-[3-(4-fluoro-phenyl)-5-hydroxymethyl-isoxazol-4-ylmethoxy]-pyridine-2-carboxylic acid (100 mg, 0.29 mmol) was converted, using 4-aminomorpholine instead of S-(+)-1-amino-2-propanol, to the title compound (57 mg, 41%), which was obtained as a white solid. MS: m/e=429.2 [M+H]$^+$.

50

The invention claimed is:

1. A compound of formula I,

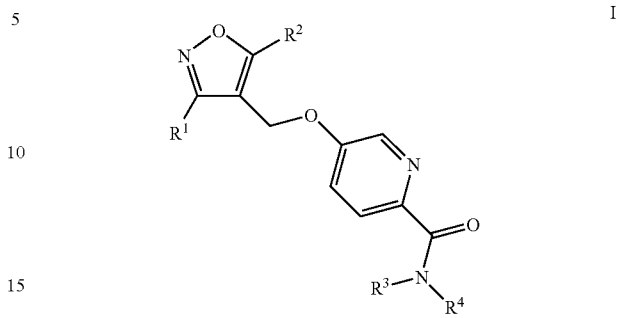

wherein
$R^1$ is selected from the group consisting of
  v) pyridinyl,
  vi) pyridinyl substituted by 1-4 substituents individually selected from acetamidyl, acetyl, acetylamino, amido, amino, carboxy, cyano, halogen, halogen-lower alkoxy, halogen-lower alkyl, hydroxy, hydroxy-lower alkyl, lower alkoxy, lower alkoxy-lower alkyl, lower alkyl, (lower alkyl,lower alkyl)N—, (lower alkyl,H)N—, nitro and lower alkyl-S(O)$_2$—;
$R^2$ is H, lower alkyl or lower alkyl substituted by 1-5 substituents individually selected from amino, halogen, halogen-lower alkoxy, hydroxy, lower alkoxy, (lower alkyl,lower alkyl)N—, (lower alkyl,H)N—, nitro and lower alkyl-S(O)$_2$—;
$R^3$ is H, lower alkyl or lower alkyl substituted by 1-5 substituents individually selected from amino, halogen, halogen-lower alkoxy, hydroxy, lower alkoxy, (lower alkyl,lower alkyl)N—, (lower alkyl,H)N—, nitro and lower alkyl-S(O)$_2$—;
$R^4$ is selected from the group consisting of
  i) H,
  ii) lower alkyl,
  iii) lower alkyl substituted by substituted by 1-5 substituents individually selected from amino, halogen, halogen-lower alkoxy, hydroxy, lower alkoxy, cycloalkyl, (lower alkyl,lower alkyl)N—, (lower alkyl,H)N—, nitro and lower alkyl-S(O)$_2$—,
  vi) cycloalkyl,
  vii) cycloalkyl substituted by 1-4 substituents individually selected from acetamidyl, acetyl, acetylamino, amido, amino, carboxy, cyano, halogen, halogen-lower alkoxy, halogen-lower alkyl, hydroxy, hydroxy-lower alkyl, lower alkoxy, lower alkoxy-lower alkyl, lower alkyl, (lower alkyl,lower alkyl)N—, (lower alkyl,H)N—, nitro and lower alkyl-S(O)$_2$—, and
  x) —NR$^5$R$^6$;
$R^5$ is H or lower alkyl; and
$R^6$ is H or lower alkyl,
or a pharmaceutically acceptable salt thereof.

2. The compound of claim 1, wherein $R^1$ is, pyridinyl or pyridinyl substituted by 1-2 halogen atoms.

3. The compound of claim 2, wherein $R^1$ is pyridinyl or fluoro-pyridinyl.

4. The compound of claim 1, wherein $R^2$ is lower alkyl or lower alkyl substituted by 1-2 hydroxy groups.

5. The compound of claim 4, wherein $R^2$ is methyl or hydroxy-methyl.

6. The compound of claim 1, wherein $R^3$ is H.

7. The compound of claim 1, wherein $R^4$ is selected from the group consisting of
  i) lower alkyl,
  ii) lower alkyl substituted by 1-2 substituents individually selected from cycloalkyl, halogen, hydroxy and lower alkoxy,
  iv) cycloalkyl,
  v) cycloalkyl substituted by 1-2 hydroxy groups, and
  vii) —NR$^5$R$^6$, wherein R$^5$ and R$^6$ are each individually selected from lower alkyl.

8. The compound of claim 7, wherein $R^4$ is selected from the group consisting of
  i) lower alkyl, and
  ii) lower alkyl substituted by 1-2 substituents individually selected from halogen and hydroxyl.

9. The compound of claim 8, wherein $R^4$ is 2,2,2-trifluoro-ethyl, 2-hydroxy-ethyl, or isopropyl.

10. The compound of claim 1 selected from the group consisting of
  5-(5-Methyl-3-pyridin-2-yl-isoxazol-4-ylmethoxy)-pyridine-2-carboxylic acid isopropylamide,
  5-(5-Methyl-3-pyridin-2-yl-isoxazol-4-ylmethoxy)-pyridine-2-carboxylic acid (2-hydroxy-1,1-dimethyl-ethyl)-amide,
  5-(5-Methyl-3-pyridin-2-yl-isoxazol-4-ylmethoxy)-pyridine-2-carboxylic acid cyclopropylamide,
  5-(5-Methyl-3-pyridin-2-yl-isoxazol-4-ylmethoxy)-pyridine-2-carboxylic acid cyclopropyl-methyl-amide, and
  5-(5-Methyl-3-pyridin-2-yl-isoxazol-4-ylmethoxy)-pyridine-2-carboxylic acid (2,2,2-trifluoro-ethyl)-amide
  or a pharmaceutically acceptable salt thereof.

11. The compound of claim 1 selected from the group consisting of
  5-(5-Methyl-3-pyridin-2-yl-isoxazol-4-ylmethoxy)-pyridine-2-carboxylic acid (2-hydroxy-ethyl)-amide,
  5-(5-Methyl-3-pyridin-2-yl-isoxazol-4-ylmethoxy)-pyridine-2-carboxylic acid methylamide,
  5-(5-Methyl-3-pyridin-2-yl-isoxazol-4-ylmethoxy)-pyridine-2-carboxylic acid methylamide,
  5-(5-Methyl-3-pyridin-2-yl-isoxazol-4-ylmethoxy)-pyridine-2-carboxylic acid ((1S,2S)-2-hydroxy-cyclopentyl)-amide,
  5-(5-Methyl-3-pyridin-2-yl-isoxazol-4-ylmethoxy)-pyridine-2-carboxylic acid (1-hydroxymethyl-propyl)-amide,
  5-(5-Methyl-3-pyridin-2-yl-isoxazol-4-ylmethoxy)-pyridine-2-carboxylic acid ((S)-1-hydroxymethyl-propyl)-amide,
  5-(5-Methyl-3-pyridin-2-yl-isoxazol-4-ylmethoxy)-pyridine-2-carboxylic acid ((S)-2,2,2-trifluoro-1-methyl-ethyl)-amide,
  5-[3-(5-Fluoro-pyridin-2-yl)-5-methyl-isoxazol-4-ylmethoxy]-pyridine-2-carboxylic acid iso-propylamide, and
  5-[3-(5-Fluoro-pyridin-2-yl)-5-methyl-isoxazol-4-ylmethoxy]-pyridine-2-carboxylic acid (2-hydroxy-1,1-dimethyl-ethyl)-amide,
  or a pharmaceutically acceptable salt thereof.

12. The compound of claim 1 selected from the group consisting of
  5-[3-(5-Fluoro-pyridin-2-yl)-5-methyl-isoxazol-4-ylmethoxy]-pyridine-2-carboxylic acid cyclo-propylamide, and
  5-[3-(5-Fluoro-pyridin-2-yl)-5-methyl-isoxazol-4-ylmethoxy]-pyridine-2-carboxylic acid (2,2,2-trifluoro-ethyl)-amide,
  or a pharmaceutically acceptable salt thereof.

13. The compound of claim 1 selected from the group consisting of
  5-(5-Methyl-3-pyridin-2-yl-isoxazol-4-ylmethoxy)-pyridine-2-carboxylic acid isopropylamide, and
  5-(5-Methyl-3-pyridin-2-yl-isoxazol-4-ylmethoxy)-pyridine-2-carboxylic acid (2-hydroxy-ethyl)-amide,
  or a pharmaceutically acceptable salt thereof.

14. The compound of claim 1 which is
  5-(5-Methyl-3-pyridin-2-yl-isoxazol-4-ylmethoxy)-pyridine-2-carboxylic acid isopropylamide,
  or a pharmaceutically acceptable salt thereof.

15. The compound of claim 1, wherein $R^4$ is lower alkyl or lower alkyl substituted by 1-2 substituents selected from cycloalkyl, halogen, hydroxy and lower alkyl.

16. The compound of claim 15, wherein $R^4$ is 1-hydroxymethyl-propyl, 2,2,2,-trifluoro-1-methyl-ethyl, 2,2,2-trifluoro-ethyl, 2-hydroxy-1,1-dimethyl-ethyl, 2-hydroxy-ethyl, or cyclopropyl-methyl.

17. The compound of claim 1 wherein $R^4$ is cycloalkyl, or cycloalkyl substituted by 1-2 hydroxy groups.

18. A pharmaceutical composition comprising a therapeutically effective amount of a compound of formula I

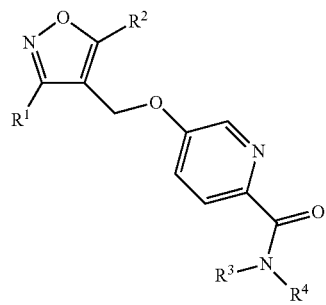

wherein
$R^1$ is selected from the group consisting of
  v) pyridinyl, and
  vi) pyridinyl substituted by 1-4 substituents individually selected from acetamidyl, acetyl, acetylamino, amido, amino, carboxy, cyano, halogen, halogen-lower alkoxy, halogen-lower alkyl, hydroxy, hydroxy-lower alkyl, lower alkoxy, lower alkoxy-lower alkyl, lower alkyl, (lower alkyl,lower alkyl)N—, (lower alkyl,H)N—, nitro and lower alkyl-S(O)$_2$—;

$R^2$ is H, lower alkyl or lower alkyl substituted by 1-5 substituents individually selected from amino, halogen, halogen-lower alkoxy, hydroxy, lower alkoxy, (lower alkyl,lower alkyl)N—, (lower alkyl,H)N—, nitro and lower alkyl-S(O)$_2$—;

$R^3$ is H, lower alkyl or lower alkyl substituted by 1-5 substituents individually selected from amino, halogen, halogen-lower alkoxy, hydroxy, lower alkoxy, (lower alkyl,lower alkyl)N—, (lower alkyl,H)N—, nitro and lower alkyl-S(O)$_2$—;

$R^4$ is selected from the group consisting of
  i) H,
  ii) lower alkyl,
  iii) lower alkyl substituted by substituted by 1-5 substituents individually selected from amino, halogen, halogen-lower alkoxy, hydroxy, lower alkoxy, cycloalkyl, (lower alkyl,lower alkyl)N—, (lower alkyl,H)N—, nitro and lower alkyl-S(O)$_2$—, vi) cycloalkyl,
vii) cycloalkyl substituted by 1-4 substituents individually selected from acetamidyl, acetyl, acetylamino, amido, amino, carboxy, cyano, halogen, halogen-lower alkoxy, halogen-lower alkyl, hydroxy, hydroxy-lower alkyl, lower alkoxy, lower alkoxy-lower alkyl, lower alkyl, (lower alkyl,lower alkyl)N—, (lower alkyl,H)N—, nitro and lower alkyl-S(O)$_2$—, and
x) —NR$^5$R$^6$;

R$^5$ is H or lower alkyl; and
R$^6$ is H or lower alkyl,
or a pharmaceutically acceptable salt thereof and a pharmaceutically acceptable carrier.

* * * * *